(12) United States Patent
Chan

(10) Patent No.: US 6,210,896 B1
(45) Date of Patent: Apr. 3, 2001

(54) MOLECULAR MOTORS

(75) Inventor: Eugene Y. Chan, Boston, MA (US)

(73) Assignee: US Genomics, Woburn, MA (US)

( * ) Notice: Subject to any disclaimer, the term of this patent is extended or adjusted under 35 U.S.C. 154(b) by 0 days.

(21) Appl. No.: 09/374,414

(22) Filed: Aug. 13, 1999

Related U.S. Application Data
(60) Provisional application No. 60/096,540, filed on Aug. 13, 1998.

(51) Int. Cl.⁷ .............................. C12Q 1/68; G01N 33/00; G01N 25/54
(52) U.S. Cl. ................................ 435/6; 436/94; 436/156; 422/82.01; 422/50
(58) Field of Search .............................. 436/94, 164, 177, 436/156; 422/82.01, 82.05, 82.08, 82.12, 50, 63, 65; 435/6

(56) References Cited

U.S. PATENT DOCUMENTS

| | | | |
|---|---|---|---|
| 4,793,705 | 12/1988 | Shera | 356/318 |
| 5,079,169 | 1/1992 | Chu et al. | 436/172 |
| 5,091,652 | 2/1992 | Mathies et al. | 250/458.1 B |
| 5,171,534 | 12/1992 | Smith et al. | 422/82.05 |
| 5,274,240 | 12/1993 | Mathies et al. | 250/458.1 |
| 5,356,776 | 10/1994 | Kambara et al. | 435/6 |
| 5,424,841 | 6/1995 | Van Gelder et al. | 356/417 |
| 5,436,130 | 7/1995 | Mathies et al. | 435/6 |
| 5,459,325 | 10/1995 | Hueton et al. | 250/458.1 |
| 5,470,707 | 11/1995 | Sasaki et al. | 435/6 |
| 5,538,848 | 7/1996 | Livak et al. | 435/5 |
| 5,538,898 | 7/1996 | Wickramasinghe et al. | 436/94 |
| 5,635,728 | 6/1997 | Cantu et al. | 250/584 |
| 5,654,419 | 8/1997 | Mathies et al. | 536/25.4 |
| 5,674,743 | 10/1997 | Ulmer | 435/287.2 |
| 5,720,928 | 2/1998 | Schwartz | 422/186 |
| 5,723,332 | 3/1998 | Chernajovsky | 435/320.1 |
| 5,795,782 | 8/1998 | Church et al. | 436/2 |
| 5,830,659 | 11/1998 | Stewart | 435/6 |
| 5,869,255 | 2/1999 | Mathies et al. | 435/6 |
| 5,888,792 | 3/1999 | Bandman et al. | 438/183 |
| 5,906,723 | 5/1999 | Mathies et al. | 204/603 |
| 5,928,869 | 7/1999 | Nadeau et al. | 435/6 |
| 5,932,442 | 8/1999 | Lal et al. | 435/69.1 |

FOREIGN PATENT DOCUMENTS

| | | |
|---|---|---|
| WO 96/30508 * | 3/1995 | (WO) . |
| WO 96/29593 | 9/1996 | (WO) . |
| WO96/ 30508A | 10/1996 | (WO) . |
| PCT/US98/ 03024 | 10/1998 | (WO) . |

OTHER PUBLICATIONS

Alexander et al., "The Reaction of Oxidizing Agents with Wool," *Biochem.*, 1951, vol. 49, pp. 129–138.

Bukrinskaya et al., "Synthesis of Protein in Paramyxovirus–Infected Cells of Susceptible and Resistant Lines at the Early Stage of Infection," D.I. Ivanovskii Institute of Virology, Academy of Medical Sciences of the USSR, Moscow. Translated From Biokhimiya, vol. 35, No. 3, pp. 516–523, May–Jun. 1970.

Wang et al, "High–resolution capillary array electrophoretic sizing of multiplexed short tandem repeat loci using energy–Transfer fluorescent primers," *Electrophoresis,* 1996, vol. 17, pp. 1485–1490.

Smith et al., "Observation of Individual DNA Molecules Undergoing Gel Electrophoresis," *Science,* vol. 243, Jan. 1989, pp. 203–206.

Schwartz et al., "Conformational dynamics of individual DNA molecules during gel eletrophoresis," *Nature,* vol. 338, Apr. 1989, pp. 520–522.

Gurrieri et al., "Imaging of Kinked Configurations of DNA Molecules Undergoing Orthogonal Field Alternating Gel Electrophoresis by Fluorescence Microscopy," *Biochemistry,* 1990, vol. 29, pp. 3396–3401.

Morozov et al., "New polyacrylamide gel–based methods of sample preparation for optical microscopy: immobilization of DNA molecules for optical mapping," *Journal of Microscopy,* 1996, vol. 183, pp. 205–214.

Meng et al., "Inhibition of Restriction Endonuclease Activity by DNA Binding Fluorochromes," *Dynamics,* vol. 13, Issue No. 6, 1996, pp. 945–951.

Meng et al., "Optical mapping of lambda bacteriophage clones using restriction endonuclease," *Nature Genetics,* vol. 9, Apr. 1995, pp. 432–438.

Printout from Kivo Genetics Web Page. May 1999 accessed.

Article by Robert A. Metzger from *Wired,* Nov. 1998, p. 4.

Davis et al., *Genet Anal Tech Appl* 1991, 8(1) pp. 1–7.

Glazer, *Curr. Opin. Biotechnol.* 1997, 8(1) pp. 94–102.

Houseal et al., *Biophys J* 1989, 56(3) pp. 507–516.

Marra et al., *Genome Res* 1996, 6(11) pp. 1118–1122.

Naktinis et al., *Cell* 1996, 84(1) pp. 137–145.

Soper et al., *J. Chromotagr A* 1999, 853(1–2) pp. 107–120.

Soper et al., *Anal Chem* 1998, 70(19) pp. 4036–4043.

(List continued on next page.)

*Primary Examiner*—John S. Brusca
*Assistant Examiner*—Stephen Siu
(74) *Attorney, Agent, or Firm*—Wolf, Greenfield & Sacks, P.C.

(57) ABSTRACT

The present invention relates to molecular motors and their use in linear analysis of polymers. In particular, molecular motors are used to move polymers with respect to a station such that specific signals arise from the interaction between the polymer and an agent at the station.

39 Claims, 3 Drawing Sheets

OTHER PUBLICATIONS

Ferreira et al., *ACS* 1995, 28, pp. 7107–7114.

Nguyen et al., *Anal Chem* 59, 2158–2161, 1987.

Periasamy et al., *J. of Computer Assisted Microscopy*, 1994, 6, pp. 1–26.

Kasianowicz et al., *Proc Natl Acad Sci USA*, 93:13770–13773, Nov. 1996.

Lee et al., *J Phys II France*, 6:195–204 (Feb. 1996).

Sung et al., *Physical Review Letters*, 74(4):783–788 (Jul. 22, 1996).

Morozov et al. "New polyacrylamide gel–based methods of sample preparation for optical microscopy: immobilization of DNA molecules for optical mapping" *Journal of Microscopy*, Sep. 1996, pp. 205–214.

Parsegian et al., *Bioscience Reports*, 15(6):503–514 (1995).

Kasianowica, Abstract, Polymer Transport in the Alpha–Hemolysin ion Channel; 6, 1996.

Bathori et al., Abstract, Th–AM–K8: DNA can be translocated across planar bilayer membrances containing Mitochondrial porin, 1998.

Haugland, Handbook of Fluorescent Probes and Research Chemicals, Sixth Edition, Chapters 8 and 9, 1996, pp. 143–200.

Alper, J., et al., "From the bioweapons trenches, new tools for battling microbes", *Science*, (1999), 248:5421:1754–5.

Nie, et al., "Probing individual molecules with confocal fluorescence microscopy", Science, ((1994), 266:5187:1018–1021.

Wu et al., "Fast Multisite Optical Measurement of Membrane Potential," Department of Physiology, Yale University School of Medicine, New Haven, CT, USA, Chapter Thirty, pp. 389–404, 1993.

Franklin et al. ,"A New Technique for Retarding Fading of Fluorescence: DPX–BME," Stain Technology, vol. 60, No. 3, 1985, pp. 125–135.

Mal'tsev et al., "Optimization of the Chromatographic Analysis of Amino Acids," Institute of High–Molecular–Weight Compounds, Academy of Sciences of the USSR, Leningrad. Translated from Zhurnal Analiticheskoi Khimii, vol. 33, No. 4, pp. 798–807, Apr., 1978.

Ambrose WP et al, "Application of single–molecule detection to DNA sequencing and sizing", Berichte Der Bunsen Gesellschaft Fur Physikalische Cemie–An International Journal of Phys Chem, Dec. 1993, vol. 97, No. 12, pp. 1535–1542.*

Nie, S et al, "Optical detection of single molecules", Annu Rev Biophys Biomol Struct, 1997, vol.26, pp. 567–596.*

Ashworth, DC et al, "Transducer mechanisms for optical biosensors Part 2. Transducer design", Comput Methods Program Biomed, 1989, vol30, No. 1, pp. 21–32.*

* cited by examiner

SEQUENCE LISTING

<160> NUMBER OF SEQ ID NOS: 4

<210> SEQ ID NO 1
<211> LENGTH: 9
<212> TYPE: DNA
<213> ORGANISM: Artificial Sequence
<220> FEATURE:
<223> OTHER INFORMATION: Synthetic sequence

<400> SEQUENCE: 1 aggcaaacg                                                                  9

<210> SEQ ID NO 2
<211> LENGTH: 10
<212> TYPE: DNA
<213> ORGANISM: Artificial Sequence
<220> FEATURE:
<223> OTHER INFORMATION: Synthetic sequence

<400> SEQUENCE: 2
agtgcaaacg                                                                10

```
<210> SEQ ID NO 3
<211> LENGTH: 16
<212> TYPE: DNA
<213> ORGANISM: Artificial Sequence
<220> FEATURE:
<223> OTHER INFORMATION: Synthetic sequence

<400> SEQUENCE: 3
acgtacgtac gtacgt                                                        16

<210> SEQ ID NO 4
<211> LENGTH: 4
<212> TYPE: DNA
<213> ORGANISM: Artificial Sequence
<220> FEATURE:
<223> OTHER INFORMATION: Synthetic sequence

<400> SEQUENCE: 4 acgt                                                                      4
```

MOLECULAR MOTORS

RELATED APPLICATIONS

This application claims priority to U.S. Provisional Patent Application No. 60/096,540, filed Aug. 13, 1998, the entire contents of which is hereby incorporated by reference.

FIELD OF THE INVENTION

The present invention relates to molecular motors and their use in linear analysis of polymers. In particular, molecular motors are used to move polymers with respect to a station such that specific signals arise from the interaction between the polymer and an agent at the station.

BACKGROUND OF THE INVENTION

Polymers are involved in diverse and essential functions in living systems. The ability to decipher the function of polymers in these systems is integral to the understanding of the role that the polymer plays within a cell. Often the function of a polymer in a living system is determined by analyzing the structure and determining the relation between the structure and the function of the polymer. By determining the primary sequence in a polymer such as a nucleic acid it is possible to generate expression maps, to determine what proteins are expressed, and to understand where mutations occur in a disease state. Because of the wealth of knowledge that may be obtained from sequencing of polymers many methods have been developed to achieve more rapid and more accurate sequencing methods.

In general DNA sequencing is currently performed using one of two methods. The first and more popular method is the dideoxy chain termination method described by Sanger et al. (1977). This method involves the enzymatic synthesis of DNA molecules terminating in dideoxynucleotides. By using the four ddNTPs, a population of molecules terminating at each position of the target DNA can be synthesized. Subsequent analysis yields information on the length of the DNA molecules and the nucleotide at which each molecule terminates (either A, C, G, or T). With this information, the DNA sequence can be determined. The second method is Maxam and Gilbert sequencing (Maxam and Gilbert, 1977), which uses chemical degradation to generate a population of molecules degraded at certain positions of the target DNA. With knowledge of the cleavage specificities of the chemical reactions and the lengths of the fragments, the DNA sequence is generated. Both methods rely on polyacrylamide gel electrophoresis and photographic visualization of the radioactive DNA fragments. Each process takes about 1–3 days. The Sanger sequencing reactions can only generate 300–800 nucleotides in one run.

Methods to improve the output of sequence information using the Sanger method also have been proposed. These Sanger-based methods include multiplex sequencing, capillary gel electrophoresis, and automated gel electrophoresis. Recently, there has also been increasing interest in developing Sanger independent methods as well. Sanger independent methods use a completely different methodology to realize the nucleotide information. This category contains the most novel techniques, which include scanning electron microscopy (STM), mass spectrometry, enzymatic luminometric inorganic pyrophosphate detection assay (ELIDA) sequencing, exonuclease sequencing, and sequencing by hybridization.

Further, several new methods have been described for carboxy terminal sequencing of polypeptides. See Inglis, A. S., Anal. Biochem. 195:183–96 (1991). Carboxy terminal sequencing methods mimic Edman degradation but involve sequential degradation from the opposite end of the polymer. See Inglis, A. S., Anal. Biochem. 195:183-96 (1991). Like Edman degradation, the carboxy-terminal sequencing methods involve chemically induced sequential removal and identification of the terminal amino acid residue.

More recently, polypeptide sequencing has been described by preparing a nested set (sequence defining set) of polymer fragments followed by mass analysis. See Chait, B. T. et al., Science 257:1885–94 (1992). Sequence is determined by comparing the relative mass difference between fragments with the known masses of the amino acid residues. Though formation of a nested (sequence defining) set of polymer fragments is a requirement of DNA sequencing, this method differs substantially from the conventional protein sequencing method consisting of sequential removal and identification of each residue. Although this method has potential in practice it has encountered several problems and has not been demonstrated to be an effective method.

SUMMARY OF THE INVENTION

The present invention relates to methods and products for linear analysis of polymers. In particular the invention is based on molecular motors and their use for guiding polymer movement during linear analysis. Recently rapid methods for analyzing polymers using linear analysis techniques have been developed. Such methods are described in co-pending PCT patent application No. PCT/US98/03024 and U.S. Ser. No. 09/134,411, the entire contents of which are hereby incorporated by reference. The method for analyzing polymers described in PCT/US98/03024 is based on the ability to examine each unit of a polymer individually. By examining each unit individually the type of unit and the position of the unit on the backbone of the polymer can be identified. This can be accomplished by positioning a unit at a station and examining a change which occurs when that unit is proximate to the station. The change can arise as a result of an interaction that occurs between the unit and the station or a partner and is specific for the particular unit. For instance if the polymer is a nucleic acid molecule and a T is positioned in proximity to a station a change which is specific for a T could occur. If on the other hand, a G is positioned in proximity to a station then a change which is specific for a G could occur. The specific change which occurs, for example, depends on the station used, the type of polymer being studied, and/or the label used. For instance the change may be an electromagnetic signal which arises as a result of the interaction.

One aspect of linear analysis techniques involves the movement of the polymer past a station in such a manner as to cause a signal that provides information about the polymer to arise. One method by which this movement can be achieved involves the use of molecular motors. A molecular motor is a molecule that interacts with a polymer and moves the polymer, unit by unit, past a station so that the polymer may be analyzed.

In one aspect the invention is a method for analyzing a polymer. The method includes the steps of exposing a plurality of individual units of a polymer to an agent selected from the group consisting of an electromagnetic radiation source, a quenching source, and a fluorescence excitation source by causing a molecular motor to move the polymer relative to the agent, and detecting signals resulting from an interaction between the units of the polymer and the agent.

In one embodiment the signal is electromagnetic radiation. In another embodiment the agent is electromagnetic radiation.

In one embodiment the molecular motor is tethered to a support. Preferably the agent is also attached to the support. In another embodiment the agent is attached to the molecular motor.

In a preferred embodiment the agent is an electromagnetic radiation source. A portion of the plurality of individual units of the polymer, in one embodiment, is labeled with a fluorophore. In another embodiment the plurality of individual units of the polymer are sequentially exposed to electromagnetic radiation by bringing the plurality of individual units in proximity to a light emissive compound and exposing the light emissive compound to electromagnetic radiation, and wherein the plurality of individual units of the polymer detectably affect emission of electromagnetic radiation from the light emissive compound. Preferably the individual units detectably affecting emission of electromagnetic radiation from the light emissive compound are labeled with a fluorophore. According to another embodiment the plurality of individual units of the polymer are sequentially exposed to electromagnetic radiation, and wherein the electromagnetic radiation detectably affects emission of electromagnetic radiation from the plurality of individual units of the polymer to produce the detectable signal.

The polymer may be any type of polymer of linked units. The type of molecular motor which can be used, however, will depend on the type of polymer. In one embodiment the polymer is a nucleic acid and the molecular motor is a polymerase. In another embodiment the polymer is a peptide and the molecular motor is a myosin.

The invention in another aspect is an article of manufacture. The article of manufacture includes a support, a molecular motor tethered to the support, and an agent selected from the group consisting of an electromagnetic radiation source, a quenching source, and a fluorescence excitation source positioned in interactive proximity with a signal station of the molecular motor. In a preferred embodiment the agent is a fluorophore.

A plurality of molecular motors is tethered to the support in one embodiment. In another embodiment the plurality of molecular motors is tethered to the support in an organized array.

In one embodiment the support is selected from the group consisting of a slide, a chip, a wall material having a channel. Preferably the support is a wall material having a channel and wherein the molecular motor is positioned at an end of the channel.

The molecular motor tethered to the support may be any type of molecular motor. Preferably the molecular motor is a nucleic acid molecular motor or a peptide molecular motor selected from the group consisting of polymerase, helicase, kinesin, dynein, actin, and myosin.

According to another aspect of the invention a molecular motor is provided. The molecular motor includes an agent positioned in interactive proximity with a signal station of the molecular motor, wherein the agent is selected from the group consisting of an electromagnetic radiation source, a quenching source, and a fluorescence excitation source. In one embodiment the molecular motor is in a solution. In another embodiment, the solution includes only a single molecular motor. Preferably the molecular motor is a nucleic acid molecular motor.

The invention in another aspect is a method for analyzing a polymer of linked units. The method includes the steps of (1) causing a labeled polymer of linked units to move relative to a molecular motor; (2) detecting sequentially polymer dependent impulses from unit labels of less than all of the linked units, and (3) storing a signature of said polymer dependent impulses detected to analyze the polymer. In some embodiments the unit label of the polymer is an extrinsic label.

In one embodiment the method is performed on a plurality of polymers simultaneously. In another embodiment the signature of polymer dependent impulses is at least 10 polymer dependent impulses.

The molecular motor can be a nucleic acid molecular motor or a peptide molecular motor. One type of nucleic acid molecular motor is a polymerase.

In one embodiment the signature of polymer dependent impulses defines the order of unit labels, the identity of each unit label being indicative of the identity of at least one unit of the polymer wherein the order of the two unit labels is the signature of said polymer dependent impulses, wherein the labeled polymer is moved linearly with respect to a station, to expose one of the unit labels to the station to produce a polymer dependent impulse which is a signature of polymer dependent impulses, and to expose the other of the unit labels to the station to produce a second detectable which is a signature of said polymer dependent impulses, different from the first polymer dependent impulse, and further comprising the step of determining the order of the polymer dependent impulses as an indication of the order of the two unit labels.

According to another embodiment the signature of polymer dependent impulses defines the distance between unit labels, the identity of each unit label being indicative of the identity of at least one unit of the polymer wherein the distance between two unit labels is the signature of said polymer dependent impulses, wherein the labeled polymer is moved linearly relative to a station to produce a characteristic polymer dependent impulse generated as each of the two unit labels passes by the station, and further comprising the step of determining the distance between the polymer dependent impulses as an indication of the distance between the two unit labels.

In other embodiments the method is a method for determining the proximity of two unit labels of the polymer wherein the proximity of the two unit labels is the signature of said polymer dependent impulses, the identity of each unit label being indicative of the identity of at least one unit of the polymer, wherein the labeled polymer is moved relative to a station to expose the two unit labels to the station to produce a characteristic polymer dependent impulse arising from a detectable physical change in the unit label or the station, and further comprising the step of measuring the amount of time elapsed between detecting each characteristic polymer dependent impulse, the amount of time elapsed being indicative of the proximity of the two unit labels.

In yet another embodiment the signature of polymer dependent impulses defines the number of unit labels.

In some embodiments all of the unit labels are detected. In other embodiments only a portion of the unit labels are detected. The polymer may be partially and randomly labeled with unit labels. In yet other embodiments all of the units of the polymer are labeled with a unit label. The labeled polymer of linked units is exposed to an agent selected from the group consisting of electromagnetic radiation, a quenching source and a fluorescence excitation source and wherein the polymer dependent impulses are produced by the interaction between a unit label of the polymer and the agent in other embodiments.

According to another aspect the invention is a method for characterizing a test polymer. The method includes the steps of obtaining polymer dependent impulses from unit labels for a plurality of labeled polymers, by making the polymers relative to a molecular motor, comparing the polymer dependent impulses of the plurality of polymers, determining the relatedness of the polymers based upon similarities between the polymer dependent impulses of the polymers, and characterizing the test polymer based upon the polymer dependent impulses of related polymers.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

The polymer dependent impulses provide many different types of structural information about the polymer. For instance the obtained polymer dependent impulses may include an order of polymer dependent impulses or the obtained polymer dependent impulses may include the time of separation between specific signals or the number of specific polymer dependent impulses.

In one important embodiment the polymer dependent impulses are obtained by moving the plurality of polymers linearly past a signal generation station.

A method for sequencing a polymer of linked units is provided according to another aspect of the invention. The method includes the steps of obtaining polymer dependent impulses from a plurality of overlapping polymers, at least a portion of each of the polymers having a sequence of linked units identical to the other of the polymers by moving the polymers linearly past a signal generation station on the molecular motor, and comparing the polymer dependent impulses to obtain a sequence of linked units which is identical in the plurality of polymers.

In one embodiment the polymer dependent impulses are optically detectable. In another embodiment the nucleic acids are labeled with an agent selected from the group consisting of an electromagnetic radiation source, a quenching source, a fluorescence excitation source, and a radiation source.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

According to another aspect the invention is a method for determining the order of units of a polymer of linked units. The method includes the steps of (1) moving the polymer linearly relative to a station using a molecular motor, (2) measuring a polymer dependent impulse generated as each of two individual units, each giving rise to a characteristic signal, pass by the station, (3) repeating steps 1 and 2 for a plurality of similar polymers, and (4) determining the order of at least the two individual units based upon the information obtained from said plurality of similar polymers.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

In one embodiment the polymer dependent impulse measured is an electromagnetic radiation signal generated. In another embodiment the two linked units are detected at the signal generation station by measuring light emission at the station. The signal generation station can be a nanochannel.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE SEQUENCES

Figure 1:
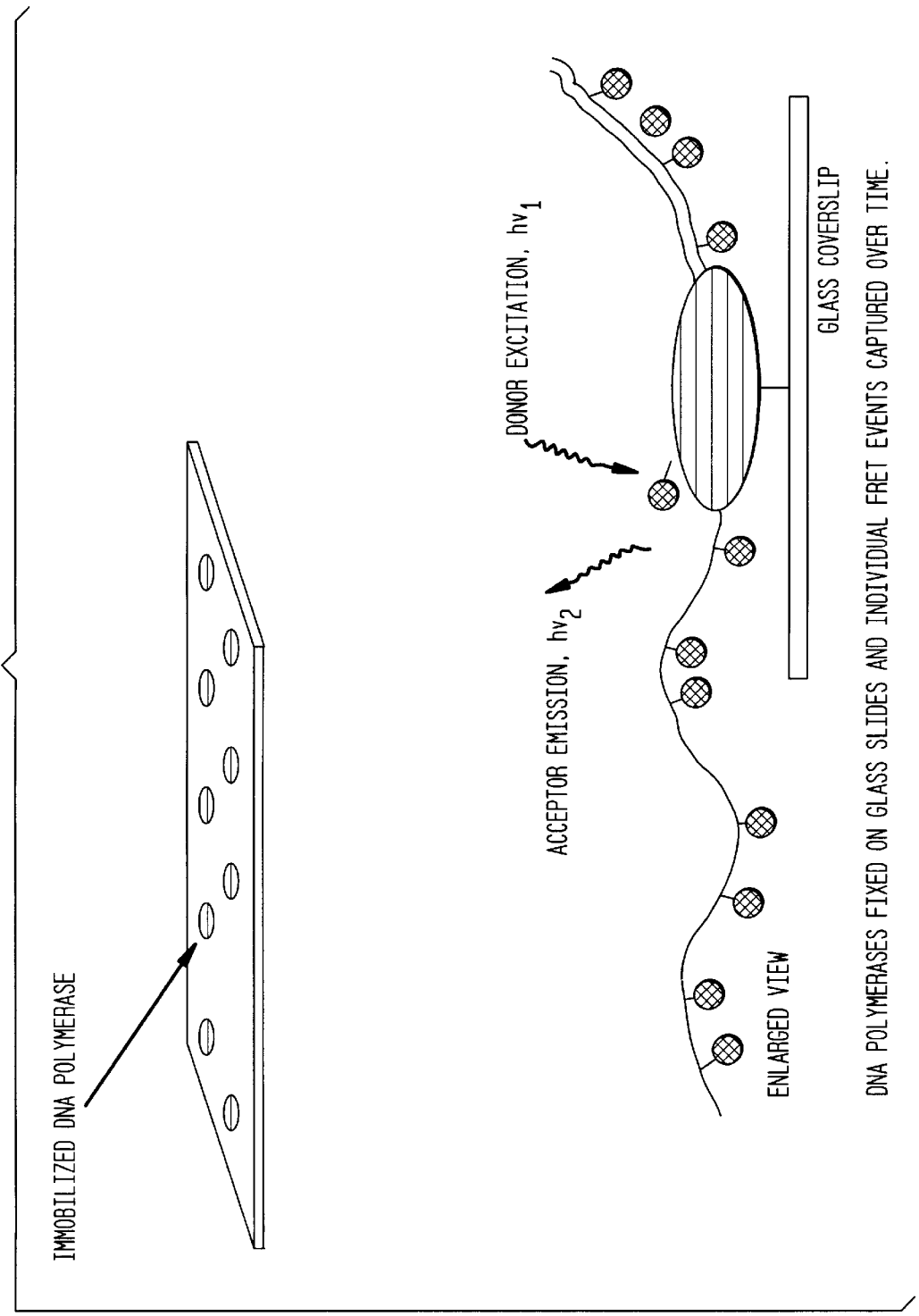
FIG. 1 is a schematic diagram of DNA polymerase fixed on a solid support and is a schematic of individual FRET events occurring on the immobilized polymerase as a DNA is moved along the polymerase.

SEQ. ID. NO. 1 is a hypothetical nucleic acid sequence.
SEQ. ID. NO. 2 is a hypothetical nucleic acid sequence.
SEQ. ID. NO. 3 is a hypothetical nucleic acid sequence.
SEQ. ID. NO. 4 is a hypothetical nucleic acid sequence.

DETAILED DESCRIPTION OF THE INVENTION

The invention relates to a method for performing linear analysis on a polymer to determine structural information about the polymer. In particular the invention is a method for analyzing a polymer by exposing labeled units of the polymer to an agent to produce a signal that arises as a result of the interaction between the agent and the labeled unit. The step of exposing the unit to the agent is accomplished with the use of a molecular motor. A molecular motor sequentially interacts with each unit of a polymer such that the unit is brought into interactive proximity with an agent where the interaction can occur.

The methods and products of the invention are useful for determining structural information about a polymer in a similar manner to the linear analysis methods described in co-pending PCT patent application No. PCT/US98/03024 and U.S. Pat. No. 09/134,411. Thus in one aspect, the methods of the invention can be used to identify one, some, or all of the units of the polymer. This is achieved by identifying the type of individual unit and its position on the backbone of the polymer by determining whether a signal detected at that particular position on the backbone is characteristic of the presence of a particular labeled unit.

In one aspect the invention is a method for analyzing a polymer. The method includes the steps of exposing a plurality of individual units of a polymer to an agent selected from the group consisting of an electromagnetic radiation source, a quenching source, and a fluorescence excitation source by causing a molecular motor to move the polymer relative to the agent, and detecting signals resulting from an interaction between the units of the polymer and the agent.

The method is a method for linear analysis, in which the signals are detected sequentially. As used herein signals are detected "sequentially" when signals from different units of a single polymer are detected spaced apart in time. Not all units need to be detected or need to generate a signal to detect signals "sequentially." When the units are sequentially exposed to the agent or station the unit and the agent or station move relative to one another. As used herein the phrase "the unit and the agent move relative to one another" means that either the unit and the agent are both moving or only one of the two is moving and the other remains stationary at least during the period of time of the interaction between the unit and the agent.

The unit and the agent are moved relative to one another by a molecular motor. A "molecular motor" as used herein is a biological molecule which physically interacts with a polymer and moves the polymer past a signal station. Preferably the molecular motor is a molecule such as a protein or protein complex that interacts with a polymer and moves with respect to the polymer along the length of the polymer. The molecular motor interacts with each unit of the polymer in a sequential manner. The physical interaction between the molecular motor and the polymer is based on molecular forces occurring between molecules such as, for instance, van der waals forces. The type of molecular motor useful according to the methods of the invention depends on the type of polymer being analyzed. For instance a molecular motor such as e.g., a DNA polymerase or a helicase is useful when the polymer is DNA, a molecular motor such as RNA polymerase is useful when the polymer is RNA, and a molecular motor such as myosin is useful for example when the polymer is a peptide such as actin. Molecular motors include, but are not limited to, helicases, RNA polymerases, DNA polymerases, kinesin, dynein, actin, and myosin. Those of ordinary skill in the art would easily be able to identify other molecular motors useful according to the invention, based on the parameters described herein.

DNA polymerases have been demonstrated to function as efficient molecular motors. Preferably the internal diameters of the regions of the polymerase which clamp onto the DNA is similar to that of double stranded DNA. Large amounts of DNA can be threaded through the clamp in a linear fashion. The overall structure of the b-subunit of DNA polymerase III holoenzyme is 80 Å in diameter with an internal diameter of ~35 Å. In comparison, a full turn of duplex B-form DNA is ~34 Å. The beta subunit fits around the DNA, in a mechanism referred to as a sliding clamp mechanism, to mediate the processive motion of the holoenzyme during DNA replication. It is well understood that the b-subunit encircles DNA during replication to confer processivity to the holoenzyme (Bloom et al., 1996; Fu et al., 1996; Griep, 1995; Herendeen and Kelly, 1996; Naktinis et al., 1996; Paz-Elizur et al., 1996; Skaliter et al., 1996). Because the sliding clamp is the mechanism of processivity for a polymerase, it necessarily means that large amounts of DNA are threaded through the clamp in a linear fashion. Several kilobases are threaded through the clamp at one time (Kornberg and Baker, 1991).

RNA polymerasees, like DNA polymerases, can also function as efficient molecular motors. The internal diameter of the region of the RNA polymerase is such that it is capable of clamping onto the RNA and moving down the RNA in a unit by unit progression. RNA polymerases include, for instance, T7 RNA polymerase, T3 or SP6 RNA polymerases, *E. coli* RNA polymerases, and the like. Suitable conditions for RNA transcription using RNA polymerases are known in the art.

Another preferred type of molecular motor is a helicase. Helicases have previously been described, e.g., see U.S. Pat. No. 5,888,792. Helicases are proteins which move along nucleic acid backbones and unwind the nucleic acid so that the processes of DNA replication, repair, recombination, transcription, mRNA splicing, translation and ribosomal assembly can take place. Helicases include both RNA and DNA helicases.

Kinesin, which is just one member of a very large family of motor proteins, was discovered in 1985 in squid axoplasm. R. D. Vale et al., Identification of a Novel Force-generating Protein, Kinesin, Involved in Microtubule-based Motility, *Cell* 42: 39–50 (1985); S. A. Endow, The Emerging Kinesin Family of Microtubule Motor Proteins, *Trends Biochem. Sci.* 16: 221 (1991); L. S. B. Goldstein, The Kinesin Superfamily: Tails of Functional Redundancy, *Trends Cell Biol.* 1: 93 (1991); R. J. Stewart et al., Identification and Partial Characterization of Six Members of the Kinesin Superfamily in Drosophila. *Proc. Nat'l Acad. Sci. USA* 88:8470 (1991). Kinesin is composed of two heavy chains (each about 120 kDa) and two light chains (each about 60 kDa). The kinesin heavy chains includes three structural domains: (a) an amino-terminal head domain, which contains the sites for ATP and microtubule binding and for motor activity; (b) a middle or stalk domain, which may form an alpha.-helical coiled coil that entwines two heavy chains to form a dimer; and (c) a carboxyl-terminal domain, which probably forms a globular tail that interacts with the light chains and possibly with vesicles and organelles. Genetic fusion of kinesin motor domain to other proteins can be accomplished while retaining motor activity in vitro. These fusion proteins include spectrin, J. T. Yang et al., The Head of Kinesin is Sufficient for Force Generation and Motility In Vitro, *Science* 249:42 (1990), glutathione S-transferase, R. J. Stewart et al., Direction of Microtubule Movement is an Intrinsic Property of the NCD and Kinesin Heavy Chain Motor Domains, *Proc. Natl Acad. Sci. USA* 90:5209 (1993), and biotin carboxyl carrier protein, E. Berliner, Microtubule Movement by a Biotinated Kinesin Bound to a Streptavidin-coated Surface, *J Biol. Chem.* 269: 8610 (1994).

Other molecular motors include dynein which is described in. M.-G. Li et al., Drosophila Cytoplasmic Dynein, a Microtubule Motor that is Asymmetrically Localized in the Oocyte, *J. Cell Biol.* 126:0 1475–1493 (1994) and myosin, which has been described in T. Q. P. Uyeda et al., *J. Molec. Biol.* 214:699–710 (1990).

The molecular motors of the invention fall into two categories, nucleic acid molecular motors and protein molecular motors. Nucleic acid molecular motors include those molecular motors that move along the backbone of a nucleic acid molecule and include, for instance, polymerases and helicases. The protein molecular motors move along the backbone of a protein or peptide, and include for instance kinesin, dynein, actin and myosin. In some embodiments the molecular motor is preferably a nucleic acid molecular motor and in other embodiments it is preferably a protein molecular motor.

Multiple polymers can be analyzed simultaneously by causing more than one polymer to move relative to respective signal stations on respective molecular motors. The polymers may be similar or distinct. If the polymers are similar, the same or different units may be detected simultaneously. The movement of the polymer may be accomplished by the molecular motor alone or may be assisted by the use of a channel, groove or ring to guide the polymer. Alternatively the molecular motor and agent may be moved and the polymer may remain stationary. For instance the agent may be attached to the molecular motor and the polymer may be secured to a surface. In this case the molecular motor with the agent attached can scan down the length of the stationary polymer.

The method of the invention is described with respect to the following non-limiting example, which is provided for illustrative purposes only. The example refers to the analysis of DNA and fluorescence, but those of ordinary skill in the art would understand that it is applicable to all polymers and all claimed detection systems. In the example, a DNA polymerase is labeled with several fluorescent molecules, e.g. donor fluorescent molecules. A DNA molecule labeled with a matching fluorophore, e.g. an acceptor fluorophore, is then used as a template for the DNA polymerase which begins to undergo primer extension. As the acceptor fluorophore moves past the donor fluorophore, fluorescence resonance energy transfer (FRET) occurs. FRET occurs when the donor and acceptor fluorophores undergo a close range interaction in the range of approximately 1 angstrom to 100 angstroms. This distance is achieved when a single nucleotide with a label passes the fluorophore on the polymerase.

FRET analysis using molecular motors can be performed on single molecules in solution or as parallel reactions on a solid planer medium. It may also be performed in parallel reactions in different solutions such as in multi-well dishes. In the embodiment in which the reaction is carried out on a planer solid medium, either the labeled polymer or the labeled molecular motor may be immobilized directly or through a linker onto the surface. If the polymer is attached to the surface, then molecular motor can be added subsequently and if the molecular motor is tethered to the surface, then the polymer may be added to initiate the reaction. In this manner, simultaneous linear reading of multiple donor-acceptor reaction sites can occur to enhance the throughput of the system. When the molecular motor is a DNA polymerase, the sequence of several kilobases of DNA can be obtained rapidly. The approximate rate of sequencing can approach 1 megabase/hour with a 1 camera system.

The preparation of fluorescently labeled enzyme and protein complexes which can serve as molecular motors, is well known in the art. The availability of multiple amine, carboxyl, and sulflfydryl sites on enzymes makes conjugation of labels to these molecules straightforward. Many proteins have been functionalized to produce fluorescent derivatives without loss of activity, including, for instance, antibodies, horseradish peroxidase, glucose oxidase, b-galactosidase, alkaline phosphatase, actin, and myosin. Molecular motors can be easily derivatized in a similar manner, without losing functional activity. Additionally, labels can be incorporated into the polymer using methods known in the art, such as those described in U.S. Ser. No. 09/134,411. For instance, the label can be incorporated into the polymer using commercially available nucleotide or amino acid polymers or as succinimydal ester derivatives which can be linked to primary amino groups.

Many fluorescent labels commercially available have functional groups which enable their conjugation to a protein such as a molecular motor and/or a polymer. These labels include, but are not limited to, fluorescein derivatives such as fluorescein isothiocyanate, NHS-fluorescein, iodoacetamidofluorescein, fluorescein-5-maleimide, SAMSA-fluorescein, fluorescein-5-thiosemicarbazide, and others. One of ordinary skill in the art has great flexibility in choosing a label for the methods of the invention because of the wide selection of conjugation techniques available for even just one type of label. Variants of rhodamines, Cy-dyes (Amersham-Pharmacia), Alexa dyes (Molecular probes), Texas Reds, and others make for a wide range of available wavelengths, photostabilities, energy transfer spectrum, and chemical compatibility. Good absorption, stable excitation, and efficient, high fluorescence quantum yield are important characteristics of the label.

As an example of fluorescent conjugation, fluorescein isothiocyanate (FITC) conjugation to a molecular motor is described. Fluorescein isothiocyanate is a prototypical fluorescent dye. It exists in two structural isomers, one modified in the lower ring at the 5-position or the 6-position. The two isoforms are optically equivalent in terms of fluorescent properties. The isothiocyanate group reacts with nucleophiles such as amines and sulfhydryls, however the only stable product is with primary amine groups such as the E- and N-terminal amines in proteins. The reaction between the isothiocyanate group and FITC yields a thiourea linkage and no leaving group. FITC is dissolved in DMF as a stock solution and then added to the aqueous reaction mixture at a pH above 6. Storage is at $-20°$ C., protected from light, and under desiccated conditions. Absorbance maximum of FITC is at 495 um and the emission maximum is at 520 nm. The solution of enzyme is usually prepared in 0.1M sodium carbonate, pH 9, and at a concentration of at least 2 mg/ml. The FITC is dissolved to a stock in DMSO/DMF at a concentration of 1 mg/ml and protected from light. In a darkened laboratory, 50–100 ul of the FITC solution is added to each milliliter of protein solution (assuming 2 mg/ml). The reaction is overnight at $4°$ C. The reaction is stopped by the addition of ammonium chloride to a final concentration of 50 mM. The remaining isothiocyanate groups are blocked after two additional hours. The derivative is purified using gel filtration with a PBS buffer.

In a preferred embodiment the fluorescent dye and its energy transfer pair is carefully selected to maximize signal production. This can be accomplished by considering the parameters described by the formula set forth below. Fluorescence energy transfer (FRET) directly related to the spectral overlap of the donor fluorescence emission and the acceptor fluorescence absorbance is determined as J, the normalized spectral overlap of the donor emission (fD) acceptor absorption ($\epsilon_A$), 90 is the quantum efficiency (or quantum yield) for donor emission in the absence of acceptor (90 is the number of photons emitted divided by number of photons absorbed), n is the index of refraction (typically 1.3–1.4), and ($\kappa C^2$ is a geometric factor related to the relative angle of the two transition dipoles. The equation which summarizes the importance of the normalized spectral overlap is given as:

$$J = \int \epsilon A(\lambda) fD(\lambda) \lambda^4 d\lambda / \int fD(\lambda) d\lambda$$

The J factor is especially important in the determination of the Forster energy transfer distance which is the distance at which energy transfer from donor fluorophore to acceptor fluorophore is 50%. The Forster distance also determines the resolution of the FRET sequencing method. In general the Forster distance can be varied to be between as small as 5 angstroms and 100 angstroms.

We have considered these variables in our choice of the optimal donor-acceptor pair for use in our FRET sequencing system. The J factor is important, but there are additional factors which should be worked into the system for optimal performance such as 1) the sharpness of the spectral bands, 2) the lack of crosstalk between the spectral bands, 3) the ability to immobilize the chosen labels in a polymeric matrix, and 4) the ability to have a match with common labels used for incorporation into DNA.

Other factors can be considered in choosing the proper fluorescent label pair. For instance, the spectral overlap of the labels should be sufficient for energy transfer. By minimalizing direct excitation of the acceptor fluorophore crosstalk in excitation levels can be avoided. Additionally, the emission of the donor fluorophore should not interfere with the detection band from the acceptor fluorophore. In this manner, the measured fluorescent events will be suitable and indicative of the occurrence of energy transfer. Under ideal conditions, the donor and acceptor fluorescence is sharp and not subject to spectral broadening. Furthermore, there are considerations in the quantum yield, photostability, and cross-sectional areas of the labels. All of these parameters can easily be manipulated by one of skill in the art based on the known properties of known and commercially available labels.

Those of ordinary skill in the art can verify the extent of fluorescent labeling of the molecular motor and/or polymer. The level of fluorescence labeling in the fluorophore conjugated molecule is determined by either the absorbance or the fluorescence emission of the sample. The number of fluorophore molecules per molecule is called the F/M ratio. This value is measured for all preparations of enzyme-fluorophore complexes. The ideal F/M ratio is determined for the particular molecule (molecular motor or polymer) molecule-fluorophore combination. Using the known extinction coefficient of the fluorophore, a determination of the derivitization level can be made after excess of the fluorophore is removed.

The activity of the labeled molecular motors can be verified using standard assays which assess the viability of the molecular motor fluorophore complex after conjugation and purification. Various molecular motors have their own assays for activity verification. DNA polymerase and its activity after conjugation to FITC is discussed below to clarify further on this subject. This example is in no way limiting of the scope of the invention.

DNA polymerase-fluorophore complexes are checked in dideoxy sequencing reactions to verify the ability of the modified molecular motor to perform its chain extension function. Primer annealing, labeling, and termination reactions are executed to determine the length of single-stranded, dideoxy terminated products and also to assay the base accuracy of the extended products. The reaction mixtures for the four dideoxynucleotides are subjected to four color automated capillary gel electrophoresis (such as the ABI 3770) for the final analysis. Match of the sequences with the known M13 ssDNA sequencing template confirms the integrity of the polymerase-fluorophore complexes.

FIG. 1 depicts an array of molecular motors (i.e. DNA polymerases) bound to the surface of a glass slide. The polymerases are labeled with donor fluorescent molecules which have emission spectra which partially overlap the excitation spectra of the acceptor molecule. Template acceptor labeled polymer (i.e. DNA) is provided in the reaction mixture along with the appropriate extension primers. The reaction is initiated with a mixture of deoxynucleotides. The chain extension allows the acceptor on the template DNA to be moved in proximity to the donors on the polymerase. Once the acceptor comes within energy transfer proximity to the donor on the immobilized polymerase molecule, non-radiative energy occurs. Sensitized fluorescence emission from the acceptor is induced. The temporally spaced fluorescence emission from the substrates allows for interrogation of the nucleotide information about the template molecule.

Statistical analysis of the different spatially oriented molecules allow for complete and accurate reconstruction of the sequence with speed and cost-effectiveness as discussed below in more detail. The methods of the invention thus allow for much longer read lengths and the complete elimination of separation methods, required by traditional non-linear sequencing method such as Sanger sequencing.

Figure 2:
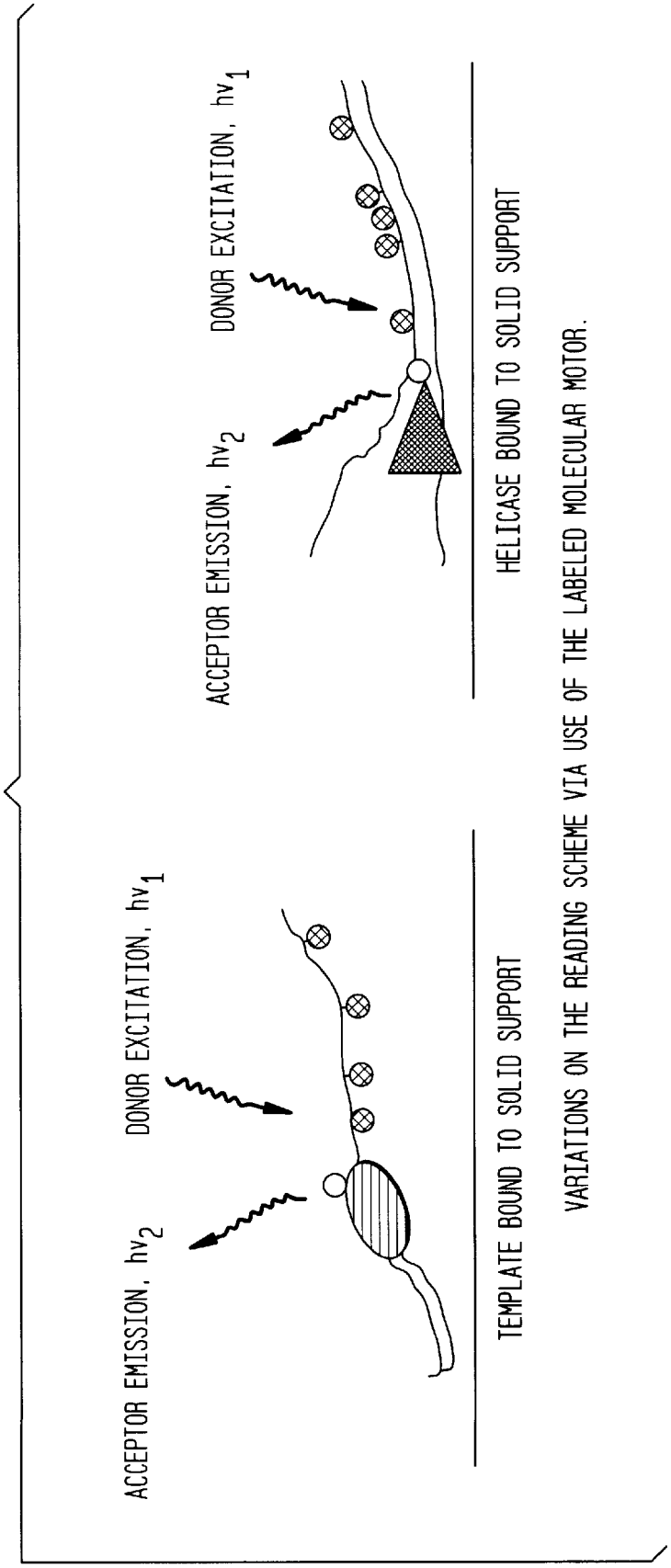
FIG. 2 is a schematic diagram of DNA polymerase fixed on a solid support through a linker and is a schematic of a helicase fixed to a solid support.

Another example of the linear analysis method of the invention is depicted in FIG. 2. In the example the template may be fixed to the glass surface and the polymerase mobile in solution. As shown in FIG. 2, the donor fluorescence molecule may be located on the DNA molecule as opposed to the acceptor. The series of interactions may be mediated by a different molecular motor such as a helicase molecule which unwinds duplex DNA. In this scenario, the helicase molecule is fluorescently tagged and allowed to unwind complexes which are asymmetrically labeled with the fluorescent molecules. The asymmetric labeling allows for the ease of deciphering the information about the polymer.

In another example the molecular motor and polymer may be in solution. The methods of analysis can be accomplished without either the molecular motor or the polymer being attached to a surface. The molecular motor and polymer can move with respect to each other in a solution. When a single molecular motor is present in the solution, individual signals arising from the interaction can be detected and analyzed by standard methods of analysis.

The methods involved in tethering the polymer or the molecular motor to a support, labeling the system components, causing the interaction between the molecular motor and the polymer, and detection methods e.g., fluorescence resonance energy transfer etc, are described herein as well as in co-pending PCT Patent Application No. PCT/US98/03024 and U.S. Ser. No. 09/134,411. Other methods for performing labeling, immobilizing biomolecules, etc are known to those of ordinary skill in the art. For instance, Schafer, D. A. et al., 1991. Transcription by single molecules of RNA polymerase observed by light microscopy. Nature 352:444-8, describes methods of labeling and detection.

The invention encompasses improved methods of analyzing a polymer by detecting a signal that results from an interaction between at least one unit of the polymer and an agent or when the unit is exposed to the station. By "analyzing" a polymer, it is meant obtaining some information about the structure of the polymer such as its size, the order of its units, its relatedness to other polymers, the identity of its units, or its presence. Since the structure and function of biological molecules are interdependent, the structural information can reveal important information about the function of the polymer.

The methods of the invention also are useful for identifying other structural properties of polymers. The structural information obtained by analyzing a polymer according to the methods of the invention may include the identification of characteristic properties of the polymer which (in turn) allows, for example, for the identification of the presence of a polymer in a sample or a determination of the relatedness of polymers, identification of the size of the polymer, identification of the proximity or distance between two or more individual units of a polymer, identification of the order of two or more individual units within a polymer, and/or identification of the general composition of the units of the polymer. Such characteristics are useful for a variety of purposes such as determining the presence or absence of a particular polymer in a sample. For instance when the polymer is a nucleic acid the methods of the invention may be used to determine whether a particular genetic sequence is expressed in a cell or tissue. The presence or absence of a particular sequence can be established by determining whether any polymers within the sample express a characteristic pattern of individual units which is only found in the polymer of interest i.e., by comparing the detected signals to a known pattern of signals characteristic of a known polymer to determine the relatedness of the polymer being analyzed to the known polymer. The entire sequence of the polymer of interest does not need to be determined in order to establish the presence or absence of the polymer in the sample. Similarly the methods may be useful for comparing the signals detected from one polymer to a pattern of signals from another polymer to determine the relatedness of the two polymers.

The proximity of or distance between two individual units of a polymer may be determined according to the methods of the invention. It is important to be able to determine the proximity of or distance between two units for several reasons. Each unit of a polymer has a specific position along the backbone. The sequence of units serves as a blueprint for a known polymer. The distance between two or more units on an unknown polymer can be compared to the blueprint of a known polymer to determine whether they are related. Additionally the ability to determine the distance between two units is important for determining how many units, if any, are between the two units of interest.

In general the methods of linear polymer analysis of the invention are performed by detecting signals arising from an interaction between a labeled unit of the polymer and an agent selected from the group consisting of an electromagnetic radiation source, a quenching source and a fluorescence excitation source. A "signal" as used herein is a detectable physical quantity which transmits or conveys information about the structural characteristics of a labeled unit of a polymer and which is capable of being detected. Preferably the physical quantity is electromagnetic radiation. The signal may arise from energy transfer, quenching, radioactivity etc. Although the signal is specific for a particular labeled unit, a polymer having more than one of a particular labeled unit will have more than one identical signal. Additionally, each labeled unit of a specific type may give rise to different signals if they have different labels.

The method used for detecting the signal depends on the type of physical quantity generated. For instance if the physical quantity is electromagnetic radiation then the signal is optically detected. An "optically detectable" signal as used herein is a light based signal in the form of electromagnetic radiation which can be detected by light detecting imaging systems.

A "plurality of polymers" is at least two polymers. A plurality of polymers in one embodiment is at least 50 polymers and in another embodiment is at least 100 polymers.

The signals may provide any type of structural information about the polymer. For instance these signals may provide the entire or portions of the entire sequence of the polymer, the order of signals, or the time of separation between signals as an indication of the distance between the labeled units.

As used herein "similar polymers" are polymers which have at least one overlapping region. Similar polymers may be a homogeneous population of polymers or a heterogenous population of polymers. A "homogeneous population" of polymers as used herein is a group of identical polymers. A "heterogenous population" of similar polymers is a group of similar polymers which are not identical but which include at least one overlapping region of identical units. An overlapping region in a nucleic acid typically consists of at least 10 contiguous nucleotides. In some cases an overlapping region consists of at least 11, 12, 13, 14, 15, 16, 17, 18, 19, 20, 21, or 22 contiguous nucleotides.

A "polymer" as used herein is a compound having a linear backbone of individual units which are linked together by linkages. In some cases the backbone of the polymer may be branched. Preferably the backbone is unbranched. The term "backbone" is given its usual meaning in the field of polymer chemistry. The polymers may be heterogeneous in backbone composition thereby containing any possible combination of polymer units linked together such as peptide-nucleic acids (which have amino acids linked to nucleic acids and have enhanced stability). In a preferred embodiment the polymers are homogeneous in backbone composition and are, for example, nucleic acids, polypeptides, polysaccharides, carbohydrates, polyurethanes, polycarbonates, polyureas, polyethyleneimines, polyarylene sulfides, polysiloxanes, polyimides, polyacetates, polyamides, polyesters, or polythioesters. In the most preferred embodiments, the polymer is a nucleic acid or a polypeptide. A "nucleic acid" as used herein is a biopolymer comprised of nucleotides, such as deoxyribose nucleic acid (DNA) or ribose nucleic acid (RNA). A polypeptide as used herein is a biopolymer comprised of linked amino acids.

As used herein with respect to linked units of a polymer, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the individual units of a particular polymer, are most common. Natural linkages include, for instance, amide, ester and thioester linkages. The individual units of a polymer analyzed by the methods of the invention may be linked, however, by synthetic or modified linkages. Polymers where the units are linked by covalent bonds will be most common but also include hydrogen bonded, etc.

The polymer is made up of a plurality of individual units. An "individual unit" as used herein is a building block or monomer which can be linked directly or indirectly to other building blocks or monomers to form a polymer. The polymer preferably is a polymer of at least two different linked units. The at least two different linked units may produce or be labeled to produce different signals, as discussed in greater detail below. The particular type of unit will depend on the type of polymer. For instance DNA is a biopolymer composed of a deoxyribose phosphate backbone composed of units of purines and pyrimidines such as adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. RNA is a biopolymer comprised of a ribose phosphate backbone composed of units of purines and pyrimidines such as those described for DNA but wherein uracil is substituted for thymidine. The DNA nucleotides may be linked to one another by their 5' or 3' hydroxyl group thereby forming an ester linkage. The RNA nucleotides may be linked to one another by their 5', 3' or 2' hydroxyl group thereby forming an ester linkage. Alternatively, DNA or RNA units having a terminal 5', 3' or 2' amino group may be linked to the other units of the polymer by the amino group thereby forming an amide linkage.

Whenever a nucleic acid is represented by a sequence of letters it will be understood that the nucleotides are in 5'→3' order from left to right and that "A" denotes adenosine, "C" denotes cytidine, "G" denotes guanosine, "T" denotes thymidine, and "U" denotes uracil unless otherwise noted.

The polymers may be native or naturally-occurring polymers which occur in nature or non-naturally occurring polymers which do not exist in nature. The polymers typically include at least a portion of a naturally occurring polymer. The polymers can be isolated or synthesized de novo. For example, the polymers can be isolated from natural sources e.g. purified, as by cleavage and gel separation or may be synthesized e.g.,(i) amplified in vitro by, for example, polymerase chain reaction (PCR); (ii) synthesized by, for example, chemical synthesis; (iii) recombinantly produced by cloning, etc.

The polymer or at least one labeled unit thereof is in a form which is capable of interacting with an agent or station to produce a signal characteristic of that interaction. The labeled unit of a polymer which is capable of undergoing such an interaction is said to be labeled. If a labeled unit of a polymer can undergo that interaction to produce a characteristic signal, then the polymer is said to be intrinsically labeled. It is not necessary that an extrinsic label be added to the polymer. If a non-native molecule, however, must be attached to the individual labeled unit of the polymer to generate the interaction producing the characteristic signal, then the polymer is said to be extrinsically labeled. The "label" may be, for example, light emitting, energy accepting, fluorescent, radioactive, or quenching. In some embodiments the labeled polymer is an extrinsically labeled polymer and in other embodiments, it is an intrinsically labeled polymer.

Many naturally occurring units of a polymer are light emitting compounds or quenchers. For instance, nucleotides of native nucleic acid molecules have distinct absorption spectra, e.g., A, G, T, C, and U have absorption maximums at 259 nm, 252 nm, 267 um, 271 nm, and 258 nm respectively. Modified units which include intrinsic labels may also be incorporated into polymers. A nucleic acid molecule may include, for example, any of the following modified nucleotide units which have the characteristic energy emission patterns of a light emitting compound or a quenching compound: 2,4-dithiouracil, 2,4-Diselenouracil, hypoxanthine, mercaptopurine, 2-aminopurine, and selenopurine.

The types of labels useful according to the methods of the invention, guidelines for selecting the appropriate labels, and methods for adding extrinsic labels to polymers are provided in more detail in co-pending PCT patent application PCT/US98/03024 and 09/134,411, which are hereby incorporated by reference.

A "labeled unit" as used herein is any labeled unit in a polymer that identifies a particular unit or units. A labeled unit includes, for instance, fluorescent markers and intrinsically and extrinsically labeled units.

A method for characterizing a test polymer is performed by obtaining polymer dependent impulses for each of a plurality of polymers, comparing the polymer dependent impulses of the plurality of polymers, determining the relatedness of the polymers based upon similarities between the polymer dependent impulses of the polymers, and characterizing the test polymer based upon the polymer dependent impulses of related polymers.

A "polymer dependent impulse" as used herein is a detectable physical quantity which transmits or conveys information about the structural characteristics of only a single unit of a polymer. The physical quantity may be in any form which is capable of being detected. For instance the physical quantity may be electromagnetic radiation, chemical conductance, electrical conductance, etc. The polymer dependent impulse may arise from energy transfer, quenching, changes in conductance, mechanical changes, resistance changes, or any other physical changes. Although the polymer dependent impulse is specific for a particular unit, a polymer having more than one of a particular labeled unit will have more than one identical polymer dependent impulse. Additionally, each unit of a specific type may give rise to different polymer dependent impulses if they have different labels.

The method used for detecting the polymer dependent impulse depends on the type of physical quantity generated. For instance if the physical quantity is electromagnetic radiation then the polymer dependent impulse is optically detected. An "optically detectable" polymer dependent impulse as used herein is a light based signal in the form of electromagnetic radiation which can be detected by light detecting imaging systems. When the physical quantity is chemical conductance then the polymer dependent impulse is chemically detected. A "chemically detected" polymer dependent impulse is a signal in the form of a change in chemical concentration or charge such as an ion conductance which can be detected by standard means for measuring chemical conductance. If the physical quantity is an electrical signal then the polymer dependent impulse is in the form of a change in resistance or capacitance.

As used herein the "relatedness of polymers" can be determined by identifying a characteristic pattern of a polymer which is unique to that polymer. For instance if the polymer is a nucleic acid then virtually any sequence of 10 contiguous nucleotides within the polymer would be a unique characteristic of that nucleic acid molecule. Any other nucleic acid molecule which displayed an identical sequence of 10 nucleotides would be a related polymer.

A "plurality of polymers" is at least two polymers. Preferably a plurality of polymers is at least 50 polymers and more preferably at least 100 polymers.

The polymer dependent impulses may provide any type of structural information about the polymer. For instance these signals may provide the entire or portions of the entire sequence of the polymer, the order of polymer dependent impulses, or the time of separation between polymer dependent impulses as an indication of the distance between the units.

The polymer dependent impulses are obtained by interaction which occurs between the unit of the polymer and the environment at a signal generation station. A "signal generation station" as used herein is a station that is an area where the unit interacts with the environment to generate a polymer dependent impulse. In some aspects of the invention the polymer dependent impulse results from contact in a defined area with an agent selected from the group consisting of electromagnetic radiation, a quenching source, and a fluorescence excitation source which can interact with the unit to produce a detectable signal. In other aspects the polymer dependent impulse results from contact in a defined area with a chemical environment which is capable of undergoing specific changes in conductance in response to an interaction with a molecule. As a molecule with a specific structure interacts with the chemical environment a change in conductance occurs. The change which is specific for the particular structure may be a temporal change, e.g., the length of time required for the conductance to change may be indicative that the interaction involves a specific structure or a physical change. For instance, the change in intensity of the interaction may be indicative of an interaction with a specific structure. In other aspects the polymer dependent impulse results from changes in capacitance or resistance caused by the movement of the unit between microelectrodes or nanoelectrodes positioned adjacent to the polymer unit. For instance the signal generation station may include microelectrodes or nanoelectrodes positioned on opposite sides of the polymer unit. The changes in resistance or conductance which occur as a result of the movement of the unit past the electrodes will be specific for the particular unit.

A method for determining the distance between two individual units is also encompassed by the invention. In order to determine the distance between two individual units of a polymer of linked units the polymer is caused to pass linearly relative to an signal generation station and a polymer dependent impulse which is generated as each of the two individual units passes by the signal generation station is measured. Each of the steps is then repeated for a plurality of similar polymers. A polymer is said to pass linearly relative to a signal generation station when each unit of the polymer passes sequentially by the signal generation station.

Each of the steps is repeated for a plurality of similar polymers to produce a data set. The distance between the two individual units can then be determined based upon the information obtained from the plurality of similar polymers by analyzing the data set.

The method also includes a method for identifying a quantity of polymers including a label. For instance, it is possible to determine the number of polymers having a specific unit or combination of units in a sample. In a sample of mRNA, for example, the number of a particular mRNA present in the sample can be determined. This is accomplished by identifying a pattern or signature characteristic of the desired mRNA molecule. The sample of RNA can then be analyzed according to the methods of the invention and the number of mRNA molecules having the specific pattern or signature can be determined.

Currently, less than 5% of the human genome has been sequenced. This translates into a small fraction of the ideal in human sequence knowledge, which is the sequence of all individuals. For an instance, for the human population, there are $1.4 \times 10^{19}$ (5 billion people x $3 \times 10^9$ bases/person). So far, only $2 \times 10^{-10}$ percent of all human genetic information is known. The rate of sequencing of the human genome by all world-wide efforts is roughly $3 \times 10^9/15$ years, or 550,000 bases/day, at a cost of >$1/base. Sequencing by the methods of the invention described herein will constitute an inordinate breakthrough in the rate of sequencing. The predicted time to complete one human genome with one machine is ~15 hours. Several dynamic arrays in parallel will be able to complete the sequence of one human genome in a fraction of an hour.

A method for sequencing a polymer of linked units is also encompassed by the invention. The method is performed by obtaining polymer dependent impulses from each of a plurality of overlapping polymers, at least a portion of each of the polymers having a sequence of linked units identical to the other of the polymers, and comparing the polymer dependent impulses to obtain a sequence of linked units which is identical in the plurality of polymers.

The plurality of overlapping polymers is a set of polymers in which each polymer has at least a portion of its sequence of linked units which is identical to the other polymers. The portion of sequence which is identical is referred to as the overlapping region and which includes at least ten contiguous units.

In another aspect of the invention the order of units of a polymer of linked units can be determined by moving the polymer linearly relative to a signal generation station and measuring a polymer dependent impulse generated as each of two individual units, each giving rise to a characteristic polymer dependent impulse pass by the signal generation station. These steps are repeated for a plurality of similar polymers and the order of at least the two individual units is determined based upon the information obtained from the plurality of similar polymers.

A method for analyzing a set of polymers, in which each of the polymers of the set is an individual polymer of linked units, is encompassed by the invention. The method involves the step of orienting the set of polymers parallel to one another, and detecting a polymer specific feature of the polymers.

The set of polymers are oriented parallel to one another. The polymers may be oriented by any means which is capable of causing the polymers to be positioned parallel to one another. For instance an electric field may be applied to the polymers to cause them to be oriented in a parallel form. Preferably the orientation step is in a solution free of gel.

A "polymer specific feature" as used herein is any structural feature of polymer which relates to its sequence. For instance a polymer specific feature includes but is not limited to information about the polymer such as the length of the polymer, the order of linked units in the polymer, the distance between units of the polymer, the proximity of units in the polymer, the sequence of one, some or all of the units of the polymer, and the presence of the polymer.

The step of detecting the polymer specific feature may be performed simultaneously for all of the polymers. This step encompasses the sequential detection of each of the units of all of the polymers. This can be accomplished by passing linearly each of the polymers relative to a plurality of signal generation stations, and detecting and distinguishing polymer dependent impulses generated as said polymers pass said signal generation stations.

The data obtained from the signals (used to refer to signals and polymer dependent impulses) may be stored in a database, or in a data file, in the memory system of the computer. The data for each polymer may be stored in the memory system so that it is accessible by the processor independently of the data for other polymers, for example by assigning a unique identifier to each polymer.

The information contained in the data and how it is analyzed depends on the number and type of labeled units that were caused to interact with the agent to generate signals. For instance if every labeled unit of a single polymer, each type of labeled unit (e.g., all the A's of a nucleic acid) having a specific type of label, is labeled then it will be possible to determine from analysis of a single polymer the order of every labeled unit within the polymer. If, however, only one of the four types of units of a nucleic acid is labeled then more data will be required to determine the complete sequence of the nucleic acid. Additionally, the method of data analysis will vary depending on whether the nucleic acid is single stranded or double stranded or otherwise complexed. Several labeling schemes and methods for analysis using the computer system data produced by those schemes are described in more detail below.

Several different strategies of labeling are possible, involving permutations of different types of units labeled, different percentage of units labeled, and single-stranded or double-stranded labeling. Set forth below are examples of labeling strategies useful according to the invention. The invention is, however, not limited to the exemplary details provided below. The labeling methods described herein and data obtained from such methods are described with reference to DNA to simplify the discussion. The invention, however, is not limited to methods of analyzing DNA, but rather may be utilized with any type of polymer which is composed of individual monomeric units. The simplest labeling scheme involves the labeling of all four nucleotides with different labels. Labeling schemes in which three, two, or even one unit are labeled, or wherein various combinations of units are labeled using labeled units which span multiple nucleotides also possible.

A four nucleotide labeling scheme can be created where the A's, C's, G's, and T's of a target DNA is labeled with different labels. Such molecule, if moved linearly past a station, will generate a linear order of signals which correspond to the linear sequence of nucleotides on the target DNA. The advantage of using a four nucleotide strategy is its ease of data interpretation and the fact that the entire sequence of labeled units can be determined from a single labeled nucleic acid. Adding extrinsic labels to all four bases, however, may cause stearic hindrance problems. In order to reduce this problem the intrinsic properties of some or all of the nucleotides may be used to label the nucleotides. As discussed above, nucleotides are intrinsically labeled because each of the purines and pyrimidines have distinct absorption spectra properties. In each of the labeling schemes described herein the nucleotides may be either extrinsically or intrinsically labeled but it is preferred that at least some of the nucleotides are intrinsically labeled when the four nucleotide labeling method is used. It is also preferred that when extrinsic labels are used with the four nucleotide labeling scheme that the labels be small and neutral in charge to reduce stearic hindrance.

A three nucleotide labeling scheme in which three of the four nucleotides are labeled may also be performed. When only three of the four nucleotides are labeled analysis of the data generated by the methods of the invention is more complicated than when all four nucleotides are labeled. The data is more complicated because the number and position of the nucleotides of the fourth unlabeled type must be determined separately. One method for determining the number and position of the fourth nucleotide utilizes analysis of two different sets of labeled nucleic acid molecules. For instance, one nucleic acid molecule may be labeled with A, C, and G, and another with C, G, and T. Analysis of the linear order of labeled nucleotides from the two sets yields sequence data. The three nucleotides chosen for each set can have many different possibilities as long as the two sets contain all four labeled nucleotides. For example, the set ACG can be paired with a set of labeled CGT, ACT or AGT.

The sequence including the fourth nucleotide also may be determined by using only a single labeled nucleic acid rather then a set of at least two differently labeled nucleic acids using a negative labeling strategy to identify the position of the fourth nucleotide on the nucleic acid. Negative labeling involves the identification of sequence information based on units which are not labeled. For instance, when three of the nucleotides of a nucleic acid molecule are labeled with a label which provides a single type of signal, the points along the nucleic acid backbone which are not labeled must be due to the fourth nucleotide. This can be accomplished by determining the distance between labeled nucleotides on a nucleic acid molecule. For example A, C, and G are labeled and the detectable signals generated indicated that the nucleic acid molecule had a sequence of AGGCAAACG (SEQ. ID. No. 1). If the distances between each of the nucleotides in the nucleic acid molecule are equivalent to the known inter-nucleotide distance for a particular combination of nucleotides except the distance between G and G is twice the normal inter-nucleotide distance then a T is positioned between the two G's and the entire molecule has a sequence of AGTGCAAACG (SEQ. ID. No. 2). The distance between nucleotides can be determined in several ways. Firstly, the nucleic acid and the station may be moved relative to one another in a linear manner and at a constant rate of speed such that a single labeled unit of the nucleic acid molecule will pass the station at a single time interval. If two time intervals elapse between detectable signals then the unlabeled nucleotide which is not capable of producing a detectable signal is present within that position. This method of determining the distance between labeled units is discussed in more detail below in reference to random one nucleotide labeling. Alternatively the nucleic acid and the station may be caused to interact with one another such that each labeled unit interacts simultaneously with a station to produce simultaneous detectable signals. Each detectable signal generated occurs at the point along the nucleic acid where the labeled unit is positioned. The distance between the detectable signals can be calculated directly to determine whether an unlabeled labeled unit is positioned anywhere along the nucleic acid molecule.

Nucleic acid molecules may also be labeled according to a two nucleotide labeling scheme. Six sets of two nucleotide labeled nucleic acid molecule can be used to resolve the data and interpret the nucleotide sequence. Ambrose et al., 1993 and Harding and Keller, 1992 have demonstrated the synthesis of large fluorescent DNA molecules with two of the nucleotides completely extrinsically labeled. The average size of the molecules were 7 kilobases. Six different combinations of two nucleotide labeling are possible using the following formula:

$$({}_nC_k) = \frac{n!}{k!(n-k)!} = \frac{4}{2!2!} = 6$$

where n nucleotides are taken k at a time. The possible combinations are AC, AG, AT, CG, CT, and GT. Knowledge of the linear order of the labels in each of the sets allows for successful reconstruction of the nucleic acid sequence. Using a 4-mer (5'ACGT'3) as a model sequence, the theory can be demonstrated. The first set, AC, gives the information that there must be a C after the A. This does not give information about the number of nucleotides intervening the A and the C nor does it give information about any G's or T's preceding the A. The second set, AG, shows that there is also a G after the A. Set AT shows there is a T after the A. From these three sets, it is then known that the target DNA is a 4-mer and that one C, one G, and one T follow the A. The subsequent sets give information on the ordering of these three nucleotides following the A. Set CG shows that G follows C. Set CT shows that T follows C. Set GT finishes the arrangement to give the final deciphered sequence of 5'ACGT'3 (SEQ ID NO. 4). In addition to the method using six labeled sets of nucleic acid molecules, the sequence can be established by combing information about the distance between labeled nucleotides generating detectable signals as described above and information obtained from fewer than six sets of two nucleotide labeled nucleic acid molecules.

A fourth labeling scheme, the random one nucleotide labeling scheme also may be used. In this method, distance information which is obtained by either population analysis and/or instantaneous rate of DNA movement is used to determine the number of nucleotides separating two labeled nucleotides. Analysis of four differently labeled target molecules yields the complete sequence.

One method of analysis with these labeling methods includes the use of complementary nucleotide information, which involves the use of two differently labeled DNA samples are required. The first sample has two of its non-complementary bases randomly labeled with the same fluorophore. Non-complementary pairs of bases are AC, AG, TC, and TG. The second sample has one of its bases randomly labeled. The nucleotide chosen for the second sample can be any of the four bases. For example, the two non-complementary bases can be chosen to be A and C. As a result, two samples are prepared, one with labeled A's and C's and another with labeled A's. The DNA can be, for example, genomically digested, end-labeled, purified, and analyzed by nanochannel FRET sequencing. The sequence-specific FRET information arising from each fragment is sorted into one of two complementary strand groups. Sorting allows population analysis to determine the positions of all the desired bases, and to thus generate sequence information from the sorted data. The first group of analyzed information yields the positions of all the A's and C's on one strand. The second group analyzed yields knowledge of all the A's and C's on one strand. The same procedure is applied to the complementary stand. Knowledge of the complementary strand's A's and C's is identical to knowledge of the T's and G's on the other stand. The result is sequence reconstruction. To cross-verify the sequence, the process can be repeated for the other pairs of non-complementary bases such as TG, TC and AG.

There are two methods of determining the distance between bases. One requires determining the instantaneous rate of DNA movement, which is readily calculated from the duration of energy transfer or quenching for a particular label. Another involves analyzing a population of target DNA molecules and its corresponding Gaussian distance distributions.

The instantaneous rate method, involves a determination of distance separation based on the known instantaneous rate of DNA movement (v) multiplied by the time of separation between signals (t). Instantaneous rate is found by measuring the time that it takes for a labeled nucleotide to pass by the interaction station. Since the length of the concentrated area of agent (d) is known (through calibration and physical measurement of the localized region of the agent, e.g., the thickness of a concentrated donor fluorophore area), the rate is simply v=d/t. Analysis of raw data demonstrating changes in energy emission patterns resulting from sequential detectable signals when plotted produces a curve which from left to right shows two energy intensity decreases, followed by two energy intensity increases. The plateau from the first energy intensity decrease (denoted $t_1$) is double that of the second plateau ($t_2$). The length of the interaction station is given as 51 Å. From this given information, the number of labeled nucleotides is known. Furthermore, the distance of separation of the two is determined by relating the rate of DNA movement to the time of the donor intensity plateaus.

The number of labeled nucleotides is simply denoted by the number of intensity decreases. If there are two intensity decreases, there must be two detectable labels on the DNA. To determine the distance of nucleotide separation, it is necessary to know the instantaneous rate of DNA movement, which is found by knowing the time for one labeled nucleotide to cross the localized region of the agent and the length of the localized region of the agent. The length of the localized region of the agent is given as 51 Å. The time for one labeled nucleotides crossing the localized region of the agent is bounded by the first intensity decrease and the first intensity increase. The rate of DNA movement is 6.8 Å/s. The nucleotide separation is derived from the time separating the labeled nucleotides ($t_1$=5 s) multiplied by the rate (6.8 Å), which is equal to 10 base pairs. As a means of cross-verification, 51 Å- $t_2$v also yields the nucleotide separation.

In the population method the entire population of labeled nucleotide is considered. Knowledge of the length of the localized region of the agent and instantaneous rate, as required for the rate method, is not necessary. Use of population analyses statistically eliminates the need for precision measurements on individual nucleic acid molecules.

An example of population analyses using five nucleic acid molecules each traversing a nanochannel is described below. Five molecules representing a population of identical DNA fragments are prepared. In a constant electric field, the time of detection between the first and second labeled nucleotide should be identical for all the DNA molecules. Under experimental conditions, these times differ slightly, leading to a Gaussian distribution of times. The peak of the Gaussian distribution is characteristic of the distance of separation (d) between two labeled nucleotides.

An additional example utilizing a population of one nucleotide randomly labeled nucleic acid molecule (six molecules represent the population) further illustrates the concept of population analysis and the determination of distance information. The nucleic acid is end-labeled to provide a reference point. With enough nucleic acid molecules, the distance between any two A's can be determined. Two molecules, when considered as a sub-population, convey the nucleotide separation molecules, distributions of 4 and 6 nucleotide separations are created. Extending the same logic to rest of the population, the positions of all the A's on the DNA can be determined. The entire sequence is generated by repeating the process for the other three bases (C, G, and T).

In addition to labeling all of one type of labeled unit in the above-described examples, it is possible to use various labeling schemes where not every nucleotide of the nucleotides or markers to be labeled is labeled, such as a one nucleotide labeling scheme where less than all of the one nucleotide are labeled. A representative population of random A-labeled fragments for a 16-mer with the sequence 5'ACGTACGTACGTACGT'3 (SEQ. ID. No. 3) is used. Each individually labeled DNA molecule has half of its A's labeled in addition to 5' and 3' end labels. With a large population of randomly labeled fragments, the distance between every successive A on the target DNA can be found. The end labels serve to identify the distance between the ends of the DNA and the first A. Repeating the same analysis for the other nucleotides generates the sequence of the 16-mer by compiling the data to identify the position of all of the As within that population of nucleic acid molecules. These steps can then be repeated using labeled units for the other nucleotides in the population of nucleic acids. The advantages of using such a method includes lack of steric effects and ease of labeling. This type of labeling is referred to as random labeling. A nucleic acid which is "randomly labeled" is one in which fewer than all of a particular type of labeled unit are labeled. It is unknown which labeled units of a particular type of a randomly labeled nucleic acid are labeled.

A similar type of analysis may be performed by labeling each of the four nucleotides incompletely but simultaneously within a population. For instance, each of the four nucleotides may be partially labeled with its own labeled unit which gives rise to a different physical characteristic, such as color, size, etc. This can be accomplished to generate a data set containing information about all of the nucleotides from a single population analysis. For instance the method may be accomplished by partially labeling two nucleotide pairs at one time. Two nucleotide labeling is possible through the lowering of steric hindrance effects by using labeled units which recognize the two nucleotides of a nucleic acid strand and which contain a label such as a single fluorescent molecule. Ambrose et al., 1993 and Harding and Keller, 1992 have demonstrated that large fluorescent nucleic acid molecules with two of the nucleotides completely labeled are possible to achieve. The average size of the molecules studied were 7 KB. Partial labeling of two and three nucleotides is possible. For instance, each of three nucleotides is partially labeled with a different labeled unit. In this case, a population of single stranded nucleic acid molecules which are partially labeled with three specific nucleotide pair combinations is generated and can be analyzed.

The methods of the invention can also be achieved using a double stranded nucleic acid. In a double stranded nucleic acid, when a single nucleotide on two of the strands is labeled, information about two nucleotides becomes available for each of the strands. For instance, in the random and partial labeling of A's, knowledge about the A's and T's becomes available. For example, a labeling strategy in which two differently labeled nucleic acid samples can be prepared. The first sample has two non-complimentary nucleotides randomly labeled with the same fluorophore. Non-complimentary pairs of nucleotides are AC, AG, TC, and TG. The second sample has one of its nucleotides randomly labeled. The nucleotide chosen for the second sample may be any one of the four nucleotides. In the example provided, the two non-complimentary nucleotides are chosen to be A and C, and the single nucleotide is chosen to be A. Two samples are prepared, one with labeled A's and C's and another with labeled A's. The nucleic acid is genomically digested, end labeled, purified, and analyzed. Such procedures are well-known to those of ordinary skill in the art. The information from each fragment is sorted into one of two complimentary strand groups. Sorting the information into different groups allows the population analysis to determine the positions of all the desired nucleotides. The first group of data provides known positions of all the A's and C's on one strand. The second group of data provides known positions of all of the A's. The combination of these two data sets reveals the position of all of the A's and C's on one strand. The same procedure may be applied to the complimentary strand to determine the positions of the A's and C's on that strand. The resultant data reveals the entire sequence for both strands of the nucleic acid, based on the assumption that the strand includes the complimentary nucleotide pairs of A and C (A:T and C:G). To cross-verify the sequence, the process can be repeated for the other pairs of non-complimentary nucleotides such as TG, TC and AG.

A single-stranded two-nucleotide labeling scheme also can be performed on double stranded DNA when two of the nucleotides on one strand of DNA are fully replaced by labeled nucleotides. To reduce the steric constraints imposed by two extrinsically labeled nucleotides while preserving the theory behind two-nucleotide labeling, it is possible to label one nucleotide fully on each of the complementary strands to achieve the same end. This method involves using double-stranded DNA in which each strand is labeled with a different label. Six differently labeled duplex DNA sets will produce a data set which is adequate to provide sequence information. Each complementary strand of DNA should have one of the nucleotides labeled. In each of the duplex DNA sets, the equivalent of two different nucleotides (possible combinations are AC, AG, AT, CG, CT, GT) are labeled. When both complementary strands have the adenines labeled, this is equivalent to the combination AT. In duplex two-nucleotide labeling, the advantage is that only one nucleotide on each strand is labeled, allowing longer labeled strands to be synthesized as compared to two-nucleotide labeling on single-stranded DNA. In practice, it has been shown that synthesis of DNA fragments with one nucleotide completely labeled can be achieved with lengths much greater than 10 kilobases (Ambrose et al., 1993; Harding and Keller, 1992).

By including more than one physical characteristic into the label, the simultaneous and overlapping reading of the nucleic acid within the same temporal frame may provide more accurate and rapid information about the positions of the labeled nucleotides than when only a single physical characteristic is included. The sample may be, for instance, labeled with different wavelength fluorophores. Each of the fluorophores can be detected separately to provide distinct readings from the same sample. For instance, the end units of a polymer may be labeled with fluorophores which emit at a first wavelength and a set of internal units may be labeled with a fluorophore which emits at a second wavelength. As the polymer is moved past the signal station both wavelengths can be detected to provide information about both sets of labels.

One use for the methods of the invention is to determine the sequence of units within a polymer. Identifying the sequence of units of a polymer, such as a nucleic acid, is an important step in understanding the function of the polymer and determining the role of the polymer in a physiological environment such as a cell or tissue. The sequencing methods currently in use are slow and cumbersome. The methods of the invention are much quicker and generate significantly more sequence data in a very short period of time.

The detectable signal is produced at a signal station. A "signal station" as used herein is a region where a portion of the polymer to be detected, e.g. the labeled unit, is exposed to, in order to produce a signal or signals. The station may be composed of any material including a gas. Preferably the station is a non-liquid material. "Non-liquid" has its ordinary meaning in the art. A liquid is a non-solid, non-gaseous material characterized by free movement of its constituent molecules among themselves but without the tendency to separate. In another preferred embodiment the station is a solid material.

The signal station is an interaction station. As used herein an "interaction station or site" is a region where a labeled unit of the polymer interacts with an agent and is positioned with respect to the agent in interactive proximity. "Interactive proximity" as used herein means that the unit and the agent are in close enough proximity whereby they can interact. The interaction station for fluorophores, for example, is that region where they are close enough so that they energetically interact to produce a signal.

The interaction station in a preferred embodiment is a region of a molecular motor where a localized agent, such as an acceptor fluorophore, attached to the molecular motor or support can interact with a polymer passing through the molecular motor. The point where the polymer passes the localized region of agent is the interaction station. As each labeled unit of the polymer passes by the agent a detectable signal is generated. The agent may be localized within the region of the channel in a variety of ways. For instance the agent may be physically attached to the molecular motor, directly or by a linker, at the site where the polymer interacts with the molecular motor. Alternatively, the molecular motor may be attached to a support and the agent may also be attached to the support, as long as the agent is attached to a region of the support by which all units of the polymer will pass. For instance, the agent may be embedded in a material or on the surface of a material that forms the wall of a channel wherein the molecular motor is attached to the wall and moves the polymer through the channel. Alternatively the agent may be a light source which is positioned a distance from the molecular motor or support but which is capable of transporting light directly to a region of the channel through a waveguide. These and other related embodiments of the invention are discussed in more detail below. The movement of the polymer may be assisted by the use of a groove or ring to guide the polymer.

Other arrangements for creating interaction stations are embraced by the invention. For example, a polymer can be passed through a molecular motor tethered to the surface of a wall or embedded in a wall, thereby bringing labeled units of the polymer sequentially to a specific location, preferably in interactive proximity to a proximate agent, thereby defining an interaction station. A molecular motor is a compound such as polymerase, helicase, or actin which interacts with the polymer and is transported along the length of the polymer past each labeled unit. Likewise, the polymer can be held from movement and a reader can be moved along the polymer, the reader being a molecular motor and having attached to it the agent.

The agent that interacts with the labeled unit of the polymer at the interaction station is selected from the group consisting of electromagnetic radiation, a quenching source, and a fluorescence excitation source. "Electromagnetic radiation" as used herein is energy produced by electromagnetic waves. Electromagnetic radiation may be in the form of a direct light source or it may be emitted by a light emissive compound such as a donor fluorophore. "Light" as used herein includes electromagnetic energy of any wavelength including visible, infrared and ultraviolet.

As used herein, a quenching source is any entity which alters or is capable of altering a property of a light emitting source. The property which is altered can include intensity fluorescence lifetime, spectra, fluorescence, or phosphorescence.

A fluorescence excitation source as used herein is any entity capable of fluorescing or giving rise to photonic emissions (i.e. electromagnetic radiation, directed electric field, temperature, fluorescence, radiation, scintillation, physical contact, or mechanical disruption.) For instance, when the labeled unit is labeled with a radioactive compound the radioactive emission causes molecular excitation of an agent that is a scintillation layer which results in fluorescence.

When a labeled unit of the polymer is exposed to the agent the interaction between the two produces a signal. The signal provides information about the polymer. For instance if all labeled units of a particular type, e.g., all of the alanines, of a protein polymer are labeled (intrinsic or extrinsic) with a particular light emissive compound then when a signal characteristic of that light emissive compound is detected upon interaction with the agent the signal signifies that an alanine residue is present at that particular location on the polymer. If each type of labeled unit e.g., each type of amino acid is labeled with a different light emissive compound having a distinct light emissive pattern then each amino acid will interact with the agent to produce a distinct signal. By determining what each signal for each labeled unit of the polymer is, the sequence of units can be determined.

The interaction between the labeled unit and the agent can take a variety of forms, but does not require that the labeled unit and the agent physically contact one another. Examples of interactions are as follows. A first type of interaction involves the agent being electromagnetic radiation and the labeled unit of the polymer being a light emissive compound (either intrinsically or extrinsically labeled with a light emissive compound). When the light emissive labeled unit is contacted with electromagnetic radiation (such as by a laser beam of a suitable wavelength or electromagnetic radiation emitted from a donor fluorophore), the electromagnetic radiation causes the light emissive compound to emit electromagnetic radiation of a specific wavelength. The signal is then measured. The signal exhibits a characteristic pattern of light emission and thus indicates that a particular labeled unit of the polymer is present. In this case the labeled unit of the polymer is said to "detectably affect the emission of the electromagnetic radiation from the light emissive compound."

A second type of interaction involves the agent being a fluorescence excitation source and the labeled unit of the polymer being a light emissive or a radioactive compound. When the light emissive labeled unit is contacted with the fluorescence excitation source, the fluorescence excitation source causes the light emissive compound to emit electromagnetic radiation of a specific wavelength. When the radioactive labeled unit is contacted with the fluorescence excitation source, the nuclear radiation emitted from the labeled unit causes the fluorescence excitation source to emit electromagnetic radiation of a specific wavelength. The signal then is measured.

A variation of these types of interaction involves the presence of a third element of the interaction, a proximate compound which is involved in generating the signal. For example, a labeled unit may be labeled with a light emissive compound which is a donor fluorophore and a proximate compound can be an acceptor fluorophore. If the light emissive compound is placed in an excited state and brought proximate to the acceptor fluorophore, then energy transfer will occur between the donor and acceptor, generating a signal which can be detected as a measure of the presence of the labeled unit which is light emissive. The light emissive compound can be placed in the "excited" state by exposing it to light (such as a laser beam) or by exposing it to a fluorescence excitation source.

Another interaction involves a proximate compound which is a quenching source. In this instance, the light emissive labeled unit is caused to emit electromagnetic radiation by exposing it to light. If the light emissive compound is placed in proximity to a quenching source, then the signal from the light emissive labeled unit will be altered.

A set of interactions parallel to those described above can be created wherein, however, the light emissive compound is the proximate compound and the labeled unit is either a quenching source or an acceptor source. In these instances the agent is electromagnetic radiation emitted by the proximate compound, and the signal is generated, characteristic of the interaction between the labeled unit and such radiation, by bringing the labeled unit in interactive proximity with the proximate compound.

The mechanisms by which each of these interactions produces a detectable signal is known in the art. For exemplary purposes the mechanism by which a donor and acceptor fluorophore interact according to the invention to produce a detectable signal including practical limitations which are known to result from this type of interaction and methods of reducing or eliminating such limitations is set forth below.

Another preferred method of analysis of the invention involves the use of radioactively labeled polymers. The type of radioactive emission influences the type of detection device used. In general, there are three different types of nuclear emission including alpha, beta, and gamma radiation. Alpha emission cause extensive ionization in matter and permit individual counting by ionization chambers and proportional counters, but more interestingly, alpha emission interacting with matter may also cause molecular excitation, which can result in fluorescence. The fluorescence is referred to as scintillation. Beta decay which is weaker than alpha decay can be amplified to generate an adequate signal. Gamma radiation arises from internal conversion of excitation energy. Scintillation counting of gamma rays is efficient and produces a strong signal. Sodium iodide crystals fluoresce with incident gamma radiation.

A "scintillation" layer or material as used herein is any type of material which fluoresces or emits light in response to excitation by nuclear radiation. Scintillation materials are well known in the art. Aromatic hydrocarbons which have resonance structures are excellent scintillators. Anthracene and stilbene fall into the category of such compounds. Inorganic crystals are also known to fluoresce. In order for these compounds to luminesce, the inorganic crystals must have small amounts of impurities, which create energy levels between valence and conduction bands. Excitation and de-excitation can therefore occur. In many cases, the de-excitation can occur through phosphorescent photon emission, leading to a long lifetime of detection. Some common scintillators include NaI (Ti), ZnS (Ag), anthracene, stilbene, and plastic phosphors.

Many methods of measuring nuclear radiation are known in the art and include devices such as cloud and bubble chamber devices, constant current ion chambers, pulse counters, gas counters (i.e., Geiger-Müller counters), solid state detectors (surface barrier detectors, lithium-drifted detectors, intrinsic germanium detectors), scintillation counters, Cerenkov detectors, etc.

Analysis of the radiolabeled polymers is identical to other means of generating signals. For example, a sample with radiolabeled A's can be analyzed by the system to determine relative spacing of A's on a sample DNA. The time between detection of radiation signals is characteristic of the polymer analyzed. Analysis of four populations of labeled DNA (A's, C's, G's, T's) can yield the sequence of the nucleic acid analyzed. The sequence of DNA can also be analyzed with a more complex scheme including analysis of a combination of dual labeled DNA and singly labeled DNA. Analysis of a and C labeled fragment followed by analysis of a labeled version of the same fragment yields knowledge of the positions of the A's and C's. The sequence is known if the procedure is repeated for the complementary strand. The system can further be used for analysis of polymer (polypeptide, RNA, carbohydrates, etc.), size, concentration, type, identity, presence, sequence and number.

The methods described above can be performed on a single polymer or on more than one polymer in order to determine structural information about the polymer.

In another preferred embodiment the signal generated by the interaction between the labeled unit and the agent results from fluorescence resonance energy transfer (FRET) between fluorophores. Either the labeled unit or the proximate compound/agent may be labeled with either the donor or acceptor fluorophore. FRET is the transfer of photonic energy between fluorophores. FRET has promise as a tool in characterizing molecular detail because of its ability to measure distances between two points separated by 10 Å to 100 Å. The angstrom resolution of FRET has been used in many studies of molecular dynamics and biophysical phenomena (for reviews see Clegg, 1995; Clegg, 1992; Selvin, 1995; and Wu and Brand, 1994). The resolving power of FRET arises because energy transfer between donor and acceptor fluorophores is dependent on the inverse sixth power of the distance between the probes. In practice, this resolution is about an order of magnitude better than that of the highest resolution electron microscope.

In order to undergo FRET, the emission spectrum of the donor overlaps with the excitation spectrum of the acceptor. The labeled unit of the polymer is specifically labeled with an acceptor fluorophore. The agent is a donor fluorophore. A laser is tuned to the excitation wavelength of the donor fluorophore. As the polymer is moved through the channel, the donor fluorophore emits its characteristic wavelength. As the acceptor fluorophore moves into interactive proximity with the donor fluorophore, the acceptor fluorophore is excited by the energy from the donor fluorophore. The consequence of this interaction is that the emission of the donor fluorophore is quenched and that of the acceptor fluorophore is enhanced.

In order to generate an optimal efficient FRET signal for detection, two conditions should be satisfied. The first condition is efficient donor emission in the absence of acceptors. The second is efficient generation of a change in either donor or acceptor emissions during FRET. Each of these are described in more detail in co-pending PCT Patent Application PCT/US98/03024 and U.S. Ser. No. 09/134, 411.

A "detectable signal" as used herein is any type of electromagnetic radiation signal which can be sensed by conventional technology. The signal produced depends on the type of station as well as the labeled unit and the proximate compound if present. In one embodiment the signal is electromagnetic radiation resulting from light emission by a labeled (intrinsic or extrinsic) labeled unit of the polymer or by the proximate compound. In another embodiment the signal is fluorescence resulting from an interaction of a radioactive emission with a scintillation layer. The detected signals may be stored in a database for analysis. One method for analyzing the stored signals is by comparing the stored signals to a pattern of signals from another polymer to determine the relatedness of the two polymers. Another method for analysis of the detected signals is by comparing the detected signals to a known pattern of signals characteristic of a known polymer to determine the relatedness of the polymer being analyzed to the known polymer. Comparison of signals is discussed in more detail below.

More than one detectable signal may be detected. For instance a first individual labeled unit may interact with the agent to produce a first detectable signal and a second individual labeled unit may interact with the agent to produce a second detectable signal different from the first detectable signal. This enables more than one type of labeled unit to be detected on a single polymer.

Once the signal is generated it can then be detected. The particular type of detection means will depend on the type of signal generated which of course will depend on the type of interaction which occurs between the labeled unit and the agent. Many interactions involved in the method of the invention will produce an electromagnetic radiation signal. Many methods are known in the art for detecting electromagnetic radiation signals, including two- and three-dimensional imaging systems. These and other systems are described in more detail in copending PCT Patent Application PCT/US98/03024 and U.S. Ser. No. 09/134,411.

Other interactions involved in the method will produce a nuclear radiation signal. As a radiolabel on a polymer passes through the defined region of detection, such as the station, nuclear radiation is emitted, some of which will pass through the defined region of radiation detection. A detector of nuclear radiation is placed in proximity of the defined region of radiation detection to capture emitted radiation signals. Many methods of measuring nuclear radiation are known in the art including cloud and bubble chamber devices, constant current ion chambers, pulse counters, gas counters (i.e., Geiger-Müller counters), solid state detectors (surface barrier detectors, lithium-drifted detectors, intrinsic germanium detectors), scintillation counters, Cerenkov detectors, etc.

Optical detectable signals are generated, detected and stored in a database the signals can be analyzed to determine structural information about the polymer. The computer may be the same computer used to collect data about the polymers, or may be a separate computer dedicated to data analysis. A suitable computer system to implement the present invention typically includes an output device which displays information to a user, a main unit connected to the output device and an input device which receives input from a user. The main unit generally includes a processor connected to a memory system via an interconnection mechanism. The input device and output device also are connected to the processor and memory system via the interconnection mechanism. Computer programs for data analysis of the detected signals are readily available from CCD manufacturers.

The methods of the invention can be accomplished using any device which produces a specific detectable signal for an individual labeled unit of a polymer as the polymer moves through a molecular motor. One type of device which enables this type of analysis is one which promotes linear movement of a polymer past an interaction station using a molecular motor, wherein the interaction station includes an agent selected from the group consisting of an electromagnetic radiation source, a quenching source, a luminescent film layer, and a fluorescence excitation source. Preferably the agent is close enough to the molecular motor and is present in an amount sufficient to detectably interact with a partner compound selected from the group consisting of a light emissive compound and a quencher being moved by the molecular motor.

Preferably the molecular motor is tethered to a support. A "support" as used herein is any solid surface, such as a slide or bead, but does not include semi-solid materials such as gels or lipid bilayers.

In another preferred embodiment, neither the molecular motor or the polymer is tethered to a support. The entire method may be performed in solution, as described above.

In another embodiment the molecular motor may be tethered to a wall material having at least one channel. This arrangement is useful for guiding the polymer as it is moved by the molecular motor. A wall material is a solid or semi-solid barrier of any dimension which is capable of supporting at least one channel. A semi-solid material is a self supporting material and may be for instance a gel material such as a polyacrylamide gel. For instance the wall material may be composed of a single support material which may be conducting or non-conducting, light permeable or light impermeable, clear or unclear. In some instances the agent is embedded within the wall material. In these instances the wall material can be solely or partially made of a non-conducting layer, a light permeable layer or a clear layer to allow the agent to be exposed to the channel formed in the wall material to allow signal generation. When the wall material is only partially made from these materials the remaining wall material may be made from a conducting, light impermeable or unclear layer, which prevent signal generation. In some cases the wall material is made up of layers of different materials. For instance, the wall material may be made of a single conducting layer and a single non-conducting layer. Alternatively the wall material may be made of a single non-conducting layer surrounded by two conducing layers. Multiple layers and various combinations of materials are encompassed by the wall material of the invention.

The agent may be tethered to the wall material in this embodiment or it may be tethered to the molecular motor.

As used herein a "luminescent film layer" is a film which is naturally luminescent or made luminescent by some means of excitation or illumination, e.g., electrooptic thin films and high index films illuminated by internal reflection.

As used herein a "material shield" is any material which prevents or limits energy transfer or quenching. Such materials include but are not limited to conductive materials, high index materials, and light impermeable materials. In a preferred embodiment the material shield is a conductive material shield. As used herein a "conductive material shield" is a material which is at least conductive enough to prevent energy transfer between donor and acceptor sources.

A "conductive material" as used herein is a material which is at least conductive enough to prevent energy transfer between a donor and an acceptor.

A "nonconductive material" as used herein is a material which conducts less than that amount that would allow energy transfer between a donor and an acceptor.

A "light permeable material" as used herein is a material which is permeable to light of a wavelength produced by the specific electromagnetic radiation, quenching source, or the fluorescence excitation source being used.

A "light impermeable material" as used herein is a material which is impermeable to light of a wavelength produced by the specific electromagnetic radiation, quenching source, or the fluorescence excitation source being used.

A "channel" as used herein is a passageway through a medium through which a polymer can pass. The channel can have any dimensions as long as a polymer is capable of passing through it. For instance the channel may be an unbranched straight cylindrical channel or it may be a branched network of interconnected winding channels. Preferably the channel is a straight nanochannel or a microchannel. A "nanochannel" as used herein is a channel having dimensions on the order of nanometers. The average diameter of a nanochannel is between 1 nm and 999 nm. A "microchannel" as used herein is a channel having dimensions on the order of micrometers. The average diameter of a microchannel is between 1 mm and 1 mm. Preferred specifications and dimensions of channels useful according to the invention are set forth in detail below. In a preferred embodiment, the channel is fixed in the wall.

An agent is attached to the wall material or the molecular motor in such a manner that it will detectably interact with a partner compound by undergoing energy transfer or quenching with the partner light emissive compound which is passing through the channel of the wall material and the molecular motor. In order to interact with the partner compound the agent can be positioned in close proximity to the channel. For example, the agent may be attached to the inside of the channel, attached to the external surface of the wall material, attached to a concentrated region of the external surface of the wall material surrounding the rim of the channel, embedded within the wall material, embedded in the form of a concentric ring in the wall material surrounding the channel, attached to a localized region of the molecular motor or attached on the surface of the molecular motor. Optionally the agent may cover the entire surface of the wall material or molecular motor or may be embedded throughout. In order to improve signal generation when the agent is not localized, a mask may be used to cover some areas of the wall material or molecular motor such that only localized regions of agent are exposed. A "mask" as used herein is an object which has openings of any size or shape. More than one agent may be attached to the wall material or motor in order to produce different signals when the agents are exposed to the partner agent.

The agent may be attached to the surface of the wall material or molecular motor by any means of performing attachment known in the art. Examples of methods for conjugating biomaterials are presented in Hermanson, G. T., *Bioconjugate Techniques,* Academic Press, Inc., San Diego, 1996, which is hereby incorporated by reference.

When the agent is attached to the surface of the wall material or molecular motor, it may be attached directly to the wall material or molecular motor or it may be attached via a linker. A "linker" as used herein with respect to the attachment of the agent is a molecule that tethers a light emitting compound or a quenching compound to the wall material or molecular motor. Linkers are well known in the art. They include hetero and homo bifunctional linkers. Commonly used linkers include alkanes of various lengths.

The agent is attached to the wall material or molecular motor in an amount sufficient to detectably interact with a partner light emissive compound. As used herein a "partner light emissive compound" is a light emissive compound as defined above but which specifically interacts with and undergoes energy transfer or quenching when positioned in close proximity to the agent. The amount of partner light emissive compound and the amount of agent required will depend on the type of agent and light emissive compound used.

As used herein a "plurality of stations" is at least two stations. Preferably a plurality of stations is at least three stations. In another preferred embodiment a plurality of stations is at least five stations.

PCT Patent Application PCT/US98/03024 and U.S. Ser. No. 09/134,411 provides a detailed description of an optimal design of a nanochannel plate having fluorophores embedded within the plate as well as other articles useful for practicing the methods of the invention. The methods of the invention are not limited, however, to the use of articles of manufacture described herein or in the priority PCT application. The examples are provided for illustrative purposes only. The methods of the invention can be performed using any system in which a plurality of labeled units of a polymer can be moved with respect to a fixed station and from which signals can be obtained.

Each of the above described nanochannels useful with the molecular motor is only an example. It is, therefore, anticipated that each of the limitations described with respect to these embodiments involving any one element or combinations of elements can be included in each nanochannel. Preparation of films having multiple layers of differing material have been described in the art, e.g., U.S. Pat. No. 5,462,467, Ferreira et. al., *Thin Solid Films* 244:806–809 (1994).

The following non-limiting Examples are presented for exemplary purposes only.

EXAMPLES

Example 1

Labeling of the Molecular Motor

There are many different means by which fluorescent labels can be attached to molecular motors. Standard reagents for labeling proteins may be used including special protein labeling reagents commercially available from Molecular Probes, Oreg. These include high quantum yield, argon ion excitable, photostable amine-dye conjugates named Alexa (Molecular Probes). Such reagents are specifically designed for the labeling of proteins. Additional protocols for protein labeling are found in *Bioconjugate Techniques* (Hermanson, 1996). Some of these include the ability to create specific functionalities. For instance, in some circumstances, it may be desirable to introduce sulfhydryl functionalities which may involve the use of 2-iminothiolane (Traut's reagent) which follows the following protocol: prepare the protein to be thiolated in a non-amine containing buffer at pH 8.0, 50 mM triethanolamine hydrochloride, 1 mM $MgCl_2$, 50 mM KCl. Dissolve Traut's reagent in water at a concentration of 2 mg/ml. React for 1 hour at room temperature. Purify the thiolated protein by dialysis or gel filtration using buffer of choice. The degree of —SH modification may be determined using the Ellman's assay. More direct labeling methods are commonly employed. One such agent includes fluorescein isothiocyanate (FITC) which can also be obtained from Molecular Probes, Oreg. Isothiocyanates react with nucleophiles such as amines, sulflhydryls, and the phenolate ion of tyrosine side chains. A general protocol for the use of FITC is as follows: (1) prepare a protein solution in 0.1M sodium carbonate, pH 9, at a concentration of at least 2 mg/ml, (2) in a darkened lab, dissolve FITC in dry DMSO at a concentration of 1 mg/ml. Do not use old FITC, as breakdown of the isothiocyanate group over time may decrease coupling efficiency. Protect from light by wrapping in aluminum foil or using amber vials, (3) in a darkened lab, slowly add 50–100 ,l of FITC solution to each milliliter of protein solution (at 2 mg/ml concentration). Gently mix the protein solution as the FITC is added, (4) react for at least 8 hours at 4° C. in the dark, (5) the reaction may be quenched by the addition of ammonium chloride to a final concentration of 50 mM. React for a further 2 hours to stop the reaction by blocking remaining isothiocyanate groups, (6) purify the derivative by gel filtration using a PBS buffer or another suitable buffer for the particular protein being modified. The use of Sephadex G-25 or similar matrices with low exclusion limits work well. To obtain complete separation, the column size should be 15–20 times the size of the applied sample. Fluorescent molecules often nonspecifically stick to the gel filtration support so reuse of the column is not recommended. Reaction with sulfhydryl groups of the protein are also possible. Examples of such reactive fluorescent dyes include 5- (and 6)-iodoacetamidofluorescein. The protocol is as follows: prepare a 20 mM 6-IAF (Pierce Chemical Company, Ill.) solution by dissolving 10.3 mg per ml of DMF, (1) prepare fresh and protect from light, (2) dissolve the protein to be modified at a concentration of 5–10 mg/ml in 20 mM 2-[tris(hydroxymethyl)methyl]amino] ethanesulfonic acid (TES), pH 7, (3) slowly add 25–50μl of the 6-IAF solution to each milliliter of the protein solution while mixing, (4) react for 2 hours at 4° C. in the dark, (5) remove excess reactant and reaction by-products by gel filtration using Sephadex G-25 or equivalent.

Example 2

Preparation of a Reaction Vessel Useful For Analysis with Molecular Motors

For bulk solution (>100 (μl) optical monitoring of the molecular motor reaction, the enzymatic reaction can take place in a reaction vessel made of high grade fused silica (i.e. HOYA quartz). The reaction vessel is a thin quartz cassette with an inlet injection hole for sample and reagent introduction. The quartz cassette is micromachined with a dry etch process for SiO2 to a depth of 1–500 Mm. The top cover of the cassette, a thin quartz piece of 150 (m thickness is thermally bonded at 1000° C. to the etched bottom portion of the cassette. An inlet port is either ultrasonically drilled in the top cover or left open the edge of the cassette. In the cassette, the highest grade fused silica is critical for low background fluorescence as well as the cleanliness of the solutions and the actual cassettes themselves. The reaction vessels are cleaned in a 5:1:1 mixture of water, ammonium hydroxide, and hydrogen peroxide, heated to 70° C. for 15 minutes. The wash is designed to remove any organic residues which give rise to background fluorescence.

In enzyme (molecular motor) or template (polymer) immobilization analysis of the complexes, a simplified reaction vessel is used which consists of high grade fused silica slide and coverslip. The enzyme or template is immobilized to the fused silica surface by different coupling means as discussed below.

Example 3

Immobilization of Biomolecules

Immobilization of molecular motors is accomplished using methods known in the art for immobilizing proteins. Immobilization of RNA transcription complexes, for instance, has been reported by Schafer et al, 1991. Briefly, transcription complexes were placed between two lines of silicone vacuum grease in the center of a borosilicate glass coverslip (Clay-Adams, No. 3223) in a humidified chamber and incubated for 15 minutes at 20° C. To remove unbound complexes, the solution over the coverslip was partially replaced 10 times by the simultaneous withdrawal of 10 μl solution and addition of 10 μl PTC buffer, and BSA was then added to a concentration of 1 mg/ml. To initiate transcription, 1 mM each of ATP, CTP, GTP, UTP was allowed to flow into the chamber. Similar protocols can be followed for the immobilization of other biomolecules such as DNA polymerase and helicases. The binding of template DNA to the solid support may be accomplished by several means including streptavidin-biotin interaction or amine-succinimidyl ester linkage. These protocols are outlined beginning with the streptavidin-biotin interaction: 2.67 μl of concentrated (15 pmol/L) are added to 7.33 μl of water. The streptavidin coated surface, obtained from Xenopore, N.J. is placed on a sponge in a petri dish in water. 10 μl of the template mixture is added to a 1 cm² area of slide. The petri dish is covered and incubated for one hour at room temperature. The glass is washed three times with 0.1M sodium phosphate pH 7.2 containing 0.15M NaCl. For the amine-succinimidyl ester linkage, the protocol follows. The succinimidyl ester derivitized surfaces are obtained from Corning Life Sciences, Mass. 200 μL of 25 picomolar DNA in phosphate buffer is added to the surface and incubated overnight at 4° C. The surface is washed three times with Tween 20 in PBS. TE buffer (10 mM Tris, pH 8, 1 mM EDTA) is added to block unreacted succinimidyl ester groups, incubating for 30 minutes at 37° C. The plate is washed three times with Tween 20 in PBS.

Additionally, the gridding/arraying of individual enzyme/ template reactions at spatially distinct locations on high quality fused silica substrate allows for highly parallel monitoring of several hundred thousand distinct sequencing reactions. Single molecular fluorescence resonance energy transfer is observed at each of the arrayed positions, leading a highly multiplexed overall throughput. A number of arraying techniques can be used to deposit the suitable microreaction mixtures at each grid location. Inkjet deposition, piezoelectric deposition, or photolithography arraying methods are possible. The fused silica surfaces are derivitized using an ethylenic double bond silane which reacts with free phosphorylated ends of DNA (U.S. Pat. No. 5,840,862). The silica surfaces are treated by UV irradiation under an oxygen atmosphere (by formation of ozone). They are then placed in a desiccator purged by argon gas. 100 μl to 500 μl of the appropriate trichlorosilane is introduced into the desiccator. The surfaces are removed after six hours incubation. A 5 μl to 10 μl DNA solution is then placed onto the surface. A fused silica coverslip is placed over the sample to seal it from evaporation. The preparation is incubated for about 1 hour at room temperature in an atmosphere saturated with water vapor. In a 0.05M MES buffer (pH=5.5), a virtually general anchoring of the DNA molecules is observed. In contrast, in a 0.01 M Tris buffer (pH=8), there are no anchored molecules. The buffer conditions and the pH allow for control of extent and amount of DNA tethering to the modified surface.

Alternatively, the enzymes are fixed onto the surface using standard protein immobilization techniques (Schafer et al., 1991). Transcription complexes (molecular motors) are placed between two lines of silicone vacuum grease in the center of a borosilicate glass coverslip (Clay-Adams, No. 3223) in a humidified chamber and incubated for 15 minutes at 20° C. To remove unbound complexes, the solution over the coverslip is partially replaced 10 times by the simultaneous withdrawal of 10 μl solution and addition of 10 μl PTC buffer. BSA is then added to a concentration of 1 mg/ml. The concentration of the complexes is adjusted so that by probability, there is less than one complex per grid location. The grid locations in this technique are determined by a hydrophobic/hydrophilic patterning area. Only the hydrophilic regions of the chip are derivitized with the enzyme complexes. The hydrophilic regions are arranged in a densely packed grid pattern with more than a million grid locations per square centimeter. To create the hydrophilic patterned areas, a porous/gridded silicone mask (General Electric RTV 615A and 615B) is placed over the glass area and subject to a gentle oxygen plasma etch using 25 mmTorr O2 at 25 sccm flow rate, 30 W for 50 seconds. The areas exposed to the oxygen etch are rendered hydrophilic and amenable to site specific immobilization of the enzyme-fluorophore complexes.

Example 4

Template Preparation and Internal Labeling

The fluorescence resonance energy transfer template DNA molecule is internally labeled using selected fluorescent bases which have been modified. The chromatide™ nucleotides (Molecular Probes, Oreg.) are suitable triphosphate analogs of the four nucleotide bases. The modified fluorescent nucleotides have a linker arm attached to a fluorophore at either the 5-position of the pyrimidines or the 8-position of the purines. The range of fluorophores include Alexa series of dyes, Texas Red, BODIPY dyes, fluorescein, tetramethylrhodamine, among others. Other triphosphate analogs of the native bases include CyDyes™ attached to native bases. These base analogs are all easily internally incorporated into DNA strands which need to be analyzed. Incorporation of the base analogs can be done using chain extension reactions such as primer-extension, nick translation, and PCR. Strands with at least two of the bases fully replaced can be synthesized to lengths greater than 10 kilobases. The ability to create long template strands for analysis is important in order to be able to enable ultra-high throughput analyses.

Example 5

Reaction Conditions for Chain Extension

Primer extension reaction are known in the art. Standard protocols include primer annealing and then chain extension. Primer extension on ss-DNA template is done using 0.5 pmol ssDNA template (as prepared above), 0.5 pmol primer, 1 $\mu$l 10× Sequenase buffer, 10 $\mu$l H2O. The mixture is pipetted up and down gently and incubated at 6 minutes at 65° C., then 20 minutes at 37° C. The annealed primer template is added to a chain extension mixture of dNTPs and a 2 $\mu$l diluted Sequanase/pyrophosphatase mix. The reaction is incubated for 5 minutes at 25° C. in the reaction vessel for analysis using FRET based correlation analysis techniques.

Example 6

Optical Arrangement and Steps for Monitoring the Reaction as it Progresses

Figure 3:
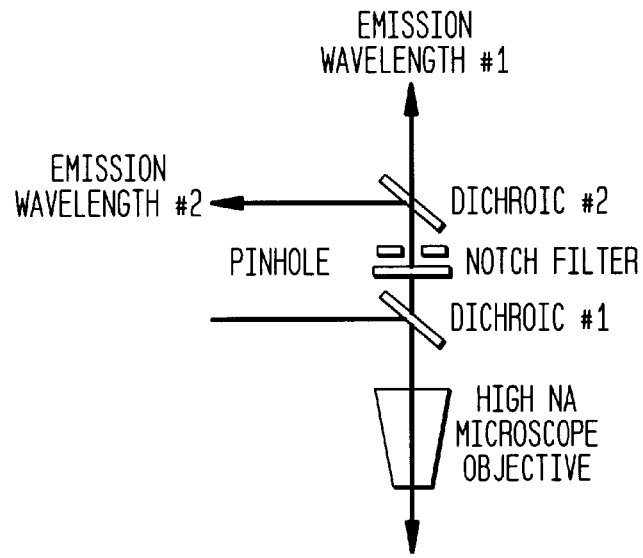
FIG. 3 is a schematic diagram of an optical system.

The detection optics of a sample system consists of a two-color scheme as shown in FIG. 3. A microscope objective, Nikon 1.4 NA 60× is used to collect the fluorescence emission from the sample. The sample is excited via traditional epiillumination by the 514 nm line of an argon ion laser (Lexel Laser 10 mW). The fluorescence light from the sample is then passed through an optional notch filter and then imaged onto a pinhole to reject out-of-focus light. The fluorescence then is split by a dichroic mirror into two parts, which are then spectrally filtered by narrow bandpasses. The resultant emission is then focused onto two high gain (200–1000) avalanche photodiodes (Advanced Photonix or EG & G). The fluorescent lablabels can include fluorescein, rhodamine, Texas Red, Cy Dyes (Amersham Pharmacia), Alexa dyes (Molecular Probes), among others. The detectors are then coupled to a multichannel scalar (EG & G) and a personal computer operating at 400 MHZ. The above scheme can be extended to additional colors by using additional dichroic beamsplitters to direct the fluorescence emission to additional avalanche photodiodes.

The combination of small confocal probe volume (0.5 femtoliter), low laser powers (1 mW to 10 mW), spatial filtering, interference filtering, and the use of high quantum efficiency detectors allows detection of as high as 4% of all emitted light from the system. The small probe volume minimizes Raman and Raleigh background as well as autofluorescence from substrates used in the preparation of samples.

FIG. 4 is a cross-sectional view of an apparatus to which the molecular motor may be attached for optical analysis. The apparatus includes a single triangular waveguide 66 and a metal electrode 85. A channel 71A formed between waveguide 66 and metal electrode 85 about 0.5 :m, is significantly larger than nanochannel 71. Triangular waveguide 66 is surrounded by metal layers on all sides and is fabricated such that the cross-hatched pattern denotes a metal layer on waveguide sides 72 and 73. Tip 70 emits evanescent waves 77, which are attenuated over a distance of only one or two wavelengths. Therefore, polymer 39 has to be pulled closer to tip 70 than electrode 85 to irradiate fluorophore 78 with evanescent waves 77.

Polymer 39 is pulled closer to tip 70 using dielectric forces created by applying an AC field to electrode 85 and waveguide 66, i.e., metal layers 64 and 74, in addition to the DC field applied across wires 98A and 98B. The AC field applied capacitively with respect to the DC field generates an inhomogeneous field in nanochannel 71. See, "Trapping of DNA in Nonuniform Oscillating Electric Fields," by Charles L. Ashbury and Ger van den Engh, Biophysical Journal Vol 74, pp 1024–1030 (1998), "Molecular Dielectrophoresis of Biopolymers," by M. Washizu, S. Suzuki, O. Kurosawa, T. Nishizaka, and T. Shinohara, in IEEE Transactions on Industry Applications, Vol 30, No 4, pp. 835–843 (1994), and "Electrostatic Manipulation of DNA in Microfabricated Structures," by M. Washizu, and O. Kurosawa, in IEEE Transactions on Industry Applications, Vol 26, No 6, pp. 1165–1172 (1990). In general, see "Dielectrophoresis: The Behavior of Neutral Matter in Nonuniform Electric Fields," by Pohl, H. A., Cambridge University Press, Cambridge, UK, 1978. The inhomogeneous field will attract polarized units of polymer 39 (e.g., DNA) to waveguide 66, as shown in FIG. 4. Thus, evanescent waves 77 again interact with fluorophore 78 selectively attached to a selected unit of polymer 39. Fluorophore 78 emits fluorescent radiation 79 propagating in all directions. Fluorescent radiation 79 is collected by waveguide 66 and conveyed to a filter optically coupled to detector 46.

Polymer alignment station 30 includes several alignment posts that have a circular cross-section and are about 1 micron in diameter. The alignment posts are spaced about 1.5 microns apart and located about 5 :m to 500 :m, and preferably about 10:m to 200:m, from nanochannel 71 depending on the length of the examined polymer. For example, when the polymer is bacteriophage T4 DNA that has about 167, 000 base pairs, the alignment posts are located about 30 :m from nanochannel 71. In general, the distance from nanochannel 71 is about one half of the expected length of polymer 39. If the distance from nanochannel 71 is significantly larger, polymer 39 may relax before it reaches nanochannel 71. On the other hand, if the distance from nanochannel 71 is significantly shorter, the ends of polymer 39 may interact with nanochannel 71 creating an error in the detection signal.

In another embodiment, the optical system includes an ultra fast, highly sensitive spectrophotometer capable of detecting fluorescence from a single fluorophore. The optical source is a mode-locked Nd:YAG laser emitting radiation of an excitation wavelength. The system uses a splitter providing a reference beam to a photodiode and a discriminator (e.g., Tennelec TC454) that provides the start pulse to a time-to-amplitude converter (e.g., Tennelec 863). The primary beam is directed through a neutral density filter that adjusts the power level. As described above, the fluorophore which interacts with the excitation light gives rise to an emission which is then collected by a detector, after being spectrally filtered by an interference filter (e.g., made by Omega Optics) and detected by an avalanche photodiode or a photomultiplier (e.g., Hamamatsu R1262MCP microchanel photomultiplier).

The microchannel photomultiplier signal is amplified by an amplifier and shaped by a discriminator (for example, Tennelec C4534 discriminator). The signal having appropriate time delays are provided to the time-to-amplitude converter (TAC). The time-gated TAC output is counted by a multiscalser and interfaced via a VME interface to system controller. System controller provides, for signal from each detector, a time-delay histogram that is characteristic for each type of the fluorescing fluorophore. Different fluorophores have different fluorescent lifetimes (i.e., the average amount of time that the molecule remains excited before returning to the ground electronic state through the emission of a fluorescent photon) that usually have an exponential probability distribution. Fluorescent lifetime is useful for identification of the fluorophore. In rapid sequencing, the system can use related labels with similar spectra but different lifetimes thus employing only one laser source emitting the excitation wavelength and one detector detecting the fluorescent radiation.

In another embodiment, the optical system uses radiation modulated at frequencies in the range of 10 MHZ to 1 GHz to characterize fluorescence of a single fluorophore located next to a polymer unit. The laser source emits a beam which is modulated at a frequency in the range of 10 MHZ to 1 GHz. The fluorescent radiation is homodyne or heterodyne detected to resolve the characteristic signal from the fluorophore, e.g., fluorescent lifetime.

Example 7

Analysis of single stranded DNA using a Molecular Motor

Single molecule data is generated from the molecular motor complex migrating along the strand of DNA, shown schematically. The data is streamed in real time to give information about the precise labeling strategy of the DNA molecule. Real-time sequence is generated from the pattern of the acceptor emissions. Excitation of the donor molecule gives rise to proximity excitation of the acceptor. Either the emission of the donor molecule is measured or the emission of the acceptor. Real-time increases in signal arises from measurement of the acceptor fluorescence and real-time decreases in signal arises from measurement of the donor fluorescence, shown in graph depicting Intensity vs Time. The raw information from single molecular analysis is directly correlated to the labeling strategy and the real-time output from the system. The information from the detectors is streamed to a databoard operating at the appropriate data rates. Software analysis in LabView or similar program yields quantitative data of DNA sequence information.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. All references, patents and patent publications that are recited in this application are incorporated in their entirety herein by reference.

I claim:

1. A method for analyzing a polymer of linked units, comprising:
exposing a plurality of individual units of a polymer of linked units to an agent selected from the group consisting of an electromagnetic radiation source, a quenching source, and a fluorescence excitation source by causing a molecular motor to move the polymer relative to the agent, and detecting signals resulting from an interaction between the linked units of the polymer and the agent.

2. The method of claim 1, wherein the molecular motor is tethered to a support.

3. The method of claim 2, wherein the agent is attached to the support.

4. The method of claim 1, wherein the agent is attached to the molecular motor.

5. The method of claim 1, wherein the signal is electromagnetic radiation.

6. The method of claim 4, wherein the agent emits electromagnetic radiation.

7. The method of claim 6, wherein a portion of the plurality of individual units of the polymer are labeled with a fluorophore.

8. The method of claim 6, wherein the plurality of individual units of the polymer are sequentially exposed to electromagnetic radiation by bringing the plurality of individual units in proximity to a light emissive compound and exposing the light emissive compound to electromagnetic radiation, and wherein the plurality of individual units of the polymer detectably affect emission of electromagnetic radiation from the light emissive compound.

9. The method of claim 6 wherein the plurality of individual units of the polymer are sequentially exposed to electromagnetic radiation, and wherein the electromagnetic radiation detectably affects emission of electromagnetic radiation from the plurality of individual units of the polymer to produce the detectable signal.

10. The method of claim 8, wherein the individual units detectably affecting emission of electromagnetic radiation from the light emissive compound are labeled with a fluorophore.

11. The method of claim 1, wherein the polymer is a nucleic acid and the molecular motor is a nucleic acid molecular motor.

12. The method of claim 1, 2, 3, 4, 5, 6, 7, 8, 9 or 10, wherein the molecular motor is a nucleic acid molecular motor that is a polymerase.

13. An article of manufacture, comprising:
a support,
a molecular motor tethered to the support, and
an agent selected from the group consisting of an electromagnetic radiation source, a quenching source, and a fluorescence excitation source positioned in interactive proximity with a signal station of the molecular motor.

14. The article of claim 13, wherein a plurality of molecular motors is tethered to the support.

15. The article of claim 14, wherein the plurality of molecular motors is tethered to the support in an organized array.

16. The article of claim 13, wherein the support is selected from the group consisting of a slide, a chip, and a wall material having a channel.

17. The article of claim 16, wherein the support is a wall material having a channel and wherein the molecular motor is positioned at an end of the channel.

18. The article of claim 13, wherein the agent is a fluorophore.

19. The article of claim 13, wherein the molecular motor is selected from the group consisting of polymerase, helicase, kinesin, dynein, actin, and myosin.

20. A nucleic acid molecular motor, wherein the nucleic acid molecular motor includes an agent selected from the group consisting of an electromagnetic radiation source, a quenching source, and a fluorescence excitation source positioned in interactive proximity with a signal station of the nucleic acid molecular motor.

21. A solution comprising the nucleic acid molecular motor of claim 20.

22. The solution of claim 21, wherein the nucleic acid molecular motor is a polymerase.

23. A method for analyzing a polymer of linked units comprising:
(1) causing a labeled polymer of linked units to move relative to a molecular motor;
(2) detecting sequentially polymer dependent impulses from linked unit labels of less than all the linked units, and (3) storing a signature of said polymer dependent impulses detected to analyze the polymer.

24. The method of claim 23, wherein the method is performed on a plurality of polymers simultaneously.

25. The method of claim 23, wherein the signature of polymer dependent impulses is at least 10 polymer dependent impulses.

26. The method of claim 23, wherein the signature of polymer dependent impulses defines the order of unit labels.

27. The method of claim 23, wherein the signature of polymer dependent impulses defines the distance between unit labels.

28. The method of claim 23, wherein the signature of polymer dependent impulses defines the number of unit labels.

29. The method of claim 23, wherein all of the unit labels are detected.

30. The method of claim 23, wherein only a portion of the unit labels are detected.

31. The method of claim 23, wherein the polymer is partially and randomly labeled with unit labels.

32. The method of claim 30, wherein all of the units of the polymer are labeled with a unit label.

33. The method of claim 23, wherein the labeled polymer of linked units is exposed to an agent selected from the group consisting of electromagnetic radiation, a quenching source and a fluorescence excitation source and wherein the polymer dependent impulses are produced by the interaction between a unit label of the polymer and the agent.

34. The method of claim 23, wherein the molecular motor is a nucleic acid molecular motor.

35. The method of claim 23, wherein the unit label of the polymer is an extrinsic label.

36. The method of claim 34, wherein the nucleic acid molecular motor is a polymerase.

37. The method of claim 23, wherein the method is a method for determining the proximity of two unit labels of the polymer wherein the proximity of the two unit labels is the signature of said polymer dependent impulses, the identity of each unit label being indicative of the identity of at least one unit of the polymer, wherein the labeled polymer is moved relative to a station to expose the two unit labels to the station to produce a characteristic polymer dependent impulse arising from a detectable physical change in the unit label or the station, and further comprising the step of measuring the amount of time elapsed between detecting each characteristic polymer dependent impulse, the amount of time elapsed being indicative of the proximity of the two unit labels.

38. The method of claim 23, wherein the method is a method for determining the order of two sequence unit labels of the polymer, the identity of each unit label being indicative of the identity of at least one unit of the polymer wherein the order of the two unit labels is the signature of said polymer dependent impulses, wherein the labeled polymer is moved linearly with respect to a station, to expose one of the unit labels to the station to produce a polymer dependent impulse which is a signature of polymer dependent impulses, and to expose the other of the unit labels to the station to produce a second detectable impulse which is a signature of said polymer dependent impulses, different from the first polymer dependent impulse, and further comprising the step of determining the order of the polymer dependent impulses as an indication of the order of the two unit labels.

39. The method of claim 23, wherein the method is a method for determining the distance between two unit labels of the polymer, the identity of each unit label being indicative of the identity of at least one unit of the polymer wherein the distance between two unit labels is the signature of said polymer dependent impulses, wherein the labeled polymer is moved linearly relative to a station to produce a characteristic polymer dependent impulse generated as each of the two unit labels passes by the station, and further comprising the step of determining the distance between the polymer dependent impulses as an indication of the distance between the two unit labels.

* * * * *

UNITED STATES PATENT AND TRADEMARK OFFICE
CERTIFICATE OF CORRECTION

PATENT NO. : 6,210,896 B1
DATED : April 3, 2001
INVENTOR(S) : Eugene Y. Chan

Figure 4A:
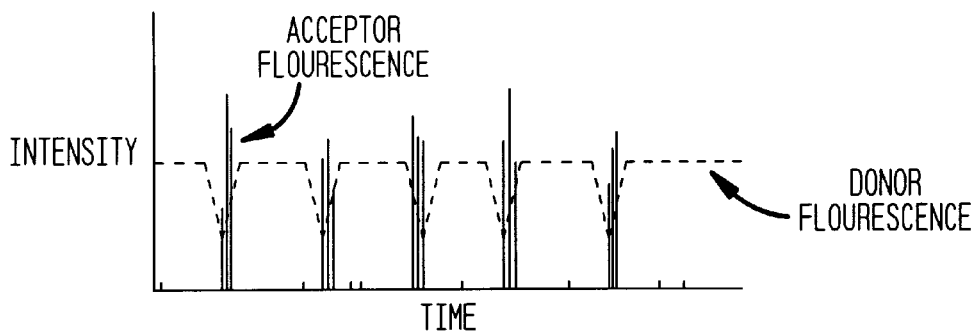
FIG. 4A is a schematic cross-sectional view of a single triangular waveguide with a nanochannel and electrodes.
Figure 4B:
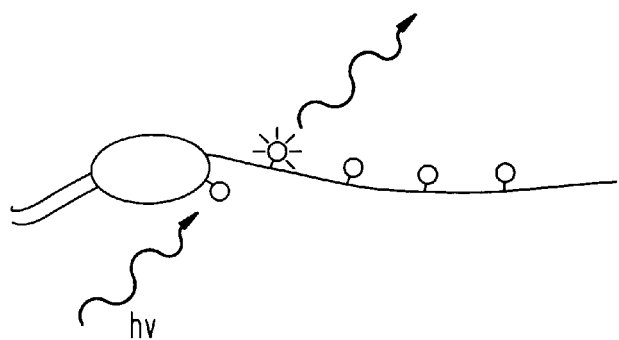
FIG. 4B is a graph depicting signal output and is a schematic of a single molecular motor migrating along a strand of DNA.

It is certified that error appears in the above-identified patent and that said Letters Patent is hereby corrected as shown below:

Column 6,
Lines 26-27, delete "FIG.4A is a schematic cross-sectional view of a single triangular wave guide with a nanochannel and electrodes.".
Line 28, delete "FIG. 4B" and replace with -- FIG. 4A --, and insert -- FIG. 4B -- between "and" and "is".

Column 36,
Lines 1-3, delete "Fig. 4 is a cross sectional view of an apparatus to which the molecular motor may be attached for optical analysis. The apparatus includes" and replace with -- An apparatus to which the molecular motor may be attached for optical analysis includes --.
Line 3, delete "66".
Line 4, delete "85" and "71A".
Line 5, delete "66" and "85".
Line 6, delete "71".
Line 7, delete "66".
Line 9, delete "72 and 73" and "70".
Line 10, delete "77".
Line 11, delete "39".
Line 12, delete "70" and "85".
Line 13, delete "78" and "77".
Line 14, delete "39" and "70".
Line 15, delete "85".
Line 16, delete "66" and "64 and 74".
Line 17, delete "98A and 98B".
Line 19, delete "71".
Line 33, delete "39" and "66".
Line 34, delete "as shown in FIG. 4" and "77".
Line 35, delete "78".
Line 36, delete "39" and "78".
Line 37, delete "79".
Line 38, delete "79" and "66".
Line 39, delete "46".
Line 40, delete "30".
Line 44, delete "71".
Line 48, delete "71".
Line 49, delete "71,".
Line 50, delete "39".
Line 51, delete "71" and "39".
Line 53, delete "71".
Line 53, delete "71".

UNITED STATES PATENT AND TRADEMARK OFFICE
CERTIFICATE OF CORRECTION

PATENT NO.   : 6,210,896 B1
DATED        : April 3, 2001
INVENTOR(S)  : Eugene Y. Chan It is certified that error appears in the above-identified patent and that said Letters Patent is hereby corrected as shown below:

<u>Column 36 (Cont'd),</u>
Line 54, delete "39" and "71".

Signed and Sealed this

Fourteenth Day of February, 2006

JON W. DUDAS
*Director of the United States Patent and Trademark Office*

UNITED STATES PATENT AND TRADEMARK OFFICE
CERTIFICATE OF CORRECTION

PATENT NO.    : 6,210,896 B1
DATED         : April 3, 2001
INVENTOR(S)   : Eugene Y. Chan It is certified that error appears in the above-identified patent and that said Letters Patent is hereby corrected as shown below:

Column 6,
Lines 26-27, delete "FIG.4A is a schematic cross-sectional view of a single triangular wave guide with a nanochannel and electrodes.".
Line 28, delete "FIG. 4B" and replace with -- FIG. 4A --, and insert -- FIG. 4B -- between "and" and "is".

Column 36,
Lines 1-3, delete "Fig. 4 is a cross sectional view of an apparatus to which the molecular motor may be attached for optical analysis. The apparatus includes" and replace with -- An apparatus to which the molecular motor may be attached for optical analysis includes --.
Line 3, delete "66".
Line 4, delete "85" and "71A".
Line 5, delete "66" and "85".
Line 6, delete "71".
Line 7, delete "66".
Line 9, delete "72 and 73" and "70".
Line 10, delete "77".
Line 11, delete "39".
Line 12, delete "70" and "85".
Line 13, delete "78" and "77".
Line 14, delete "39" and "70".
Line 15, delete "85".
Line 16, delete "66" and "64 and 74".
Line 17, delete "98A and 98B".
Line 19, delete "71".
Line 33, delete "39" and "66".
Line 34, delete "as shown in FIG. 4" and "77".
Line 35, delete "78".
Line 36, delete "39" and "78".
Line 37, delete "79".
Line 38, delete "79" and "66".
Line 39, delete "46".
Line 40, delete "30".
Line 44, delete "71".
Line 48, delete "71".
Line 49, delete "71,".
Line 50, delete "39".
Line 51, delete "71" and "39".
Line 52, delete "71".
Line 53, delete "71".

UNITED STATES PATENT AND TRADEMARK OFFICE
CERTIFICATE OF CORRECTION

PATENT NO. : 6,210,896 B1
DATED : April 3, 2001
INVENTOR(S) : Eugene Y. Chan

It is certified that error appears in the above-identified patent and that said Letters Patent is hereby corrected as shown below:

Column 36 (cont'd),
Line 54, delete "39" and "71".

This certificate supersedes Certificate of Correction issued February 14, 2006.

Signed and Sealed this

Ninth Day of May, 2006

JON W. DUDAS
*Director of the United States Patent and Trademark Office*